US011311544B2

(12) United States Patent
Grigoriadis

(10) Patent No.: US 11,311,544 B2
(45) Date of Patent: *Apr. 26, 2022

(54) TREATMENT OF CONGENITAL ADRENAL HYPERPLASIA

(71) Applicant: Neurocrine Biosciences, Inc., San Diego, CA (US)

(72) Inventor: Dimitri E. Grigoriadis, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,553

(22) Filed: Aug. 4, 2021

(65) Prior Publication Data

US 2021/0361659 A1 Nov. 25, 2021

Related U.S. Application Data

(63) Continuation of application No. 17/074,845, filed on Oct. 20, 2020, which is a continuation of application No. 16/227,127, filed on Dec. 20, 2018, now Pat. No. 10,905,690, which is a continuation of application No. 15/113,362, filed as application No. PCT/US2015/012315 on Jan. 21, 2015, now abandoned.

(60) Provisional application No. 61/929,941, filed on Jan. 21, 2014, provisional application No. 61/981,033, filed on Apr. 17, 2014, provisional application No. 62/069,155, filed on Oct. 27, 2014.

(51) Int. Cl.
| | | |
|---|---|---|
| A61K 31/519 | (2006.01) | |
| A61K 31/427 | (2006.01) | |
| A61K 31/4985 | (2006.01) | |

(52) U.S. Cl.
CPC .......... *A61K 31/519* (2013.01); *A61K 31/427* (2013.01); *A61K 31/4985* (2013.01)

(58) Field of Classification Search
CPC .................................................... A61K 31/519
USPC .......................................................... 514/250
See application file for complete search history.

(56) References Cited

U.S. PATENT DOCUMENTS

| | | | |
|---|---|---|---|
| 5,464,847 A | 11/1995 | Courtemanche et al. | |
| 6,531,475 B1 | 3/2003 | Haddach et al. | |
| 6,586,456 B1 | 7/2003 | Fontaine et al. | |
| 6,610,678 B2 | 8/2003 | Huang et al. | |
| 6,664,261 B2 | 12/2003 | Chen et al. | |
| 6,806,282 B2 | 10/2004 | Geslin et al. | |
| 8,030,304 B2 | 10/2011 | Chen et al. | |
| 8,153,127 B2 | 4/2012 | Paez-Pereda et al. | |
| 8,314,249 B2 | 11/2012 | Fazekas et al. | |
| 8,420,679 B2 | 4/2013 | Fontaine et al. | |
| 10,849,908 B2 | 12/2020 | Howerton et al. | |
| 10,905,690 B2 | 2/2021 | Grigoriadis | |
| 10,905,960 B2 * | 2/2021 | Yoneyama | G06F 3/04817 |
| 2005/0209250 A1 | 9/2005 | Romano | |
| 2006/0078623 A1 | 4/2006 | Dhoot et al. | |
| 2010/0222339 A1 | 9/2010 | Chen et al. | |
| 2017/0020877 A1 | 1/2017 | Grigoriadis | |
| 2019/0231781 A1 | 8/2019 | Grigoriadis | |
| 2021/0137926 A1 | 5/2021 | Grigoriadis | |
| 2022/0023266 A1 | 1/2022 | Father et al. | |

FOREIGN PATENT DOCUMENTS

| | | |
|---|---|---|
| JP | 4949582 | 3/2012 |
| JP | 2013-231063 | 11/2013 |
| WO | 98/08846 | 3/1998 |
| WO | 98/11075 | 3/1998 |
| WO | 99/10350 | 3/1999 |
| WO | 00/59888 | 10/2000 |
| WO | WO 03/006015 | 1/2003 |
| WO | 2006/044821 | 4/2006 |
| WO | 2006/044958 | 4/2006 |
| WO | 2006/102194 | 9/2006 |
| WO | 2006/107784 | 10/2006 |
| WO | 2006/116412 | 11/2006 |
| WO | 2006/126718 | 11/2006 |
| WO | 2007/069565 | 6/2007 |
| WO | 2007/069671 | 6/2007 |
| WO | 2007/090631 | 8/2007 |
| WO | WO 2007/105113 | 9/2007 |
| WO | 2007/137227 | 11/2007 |
| WO | 2008/036541 | 3/2008 |
| WO | 2008/036579 | 3/2008 |
| WO | 2008/051533 | 5/2008 |
| WO | 2008/082003 | 7/2008 |
| WO | 2008/083070 | 7/2008 |
| WO | 2008/136377 | 11/2008 |
| WO | 2009/008552 | 1/2009 |
| WO | 2009/144632 | 12/2009 |
| WO | 2010/014280 | 2/2010 |

(Continued)

OTHER PUBLICATIONS

Lekarev, Best Practice & Research, Clinical Endocrinology & Metabolism (2011), 25(6), 959-973.*

[No Author Listed], "Form8-K: Current Report," Securities and Exchange Commission, Washington, D.C., Apr. 5, 2000, 5 pages.

[No Author Listed], "Neurocrine announces top-line results of corticotropin releasing factor antagonist GSK561679 for treatment of major depressive disorder," Neurocrine Biosciences, Inc., Sep. 14, 2010, 1 page.

[No Author Listed], "Sanofi-Aventis: strong performance of growth platforms in Q1 2011," Sanofi Press Release, Apr. 28, 2011, 13 pages.

(Continued)

*Primary Examiner* — Nizal S Chandrakumar
(74) *Attorney, Agent, or Firm* — Fish & Richardson P.C.

(57) ABSTRACT

$CRF_1$ receptor antagonists have the potential to directly inhibit ACTH release in patients with CAH and thereby allow normalization of androgen production while using lower, more physiologic doses of hydrocortisone, and thus reducing treatment-associated side effects.

28 Claims, 6 Drawing Sheets

(56) References Cited

FOREIGN PATENT DOCUMENTS

| WO | 2010/014687 | 2/2010 |
|---|---|---|
| WO | 2010/015628 | 2/2010 |
| WO | 2010/015655 | 2/2010 |
| WO | 2010/062718 | 6/2010 |
| WO | 2010/096426 | 8/2010 |
| WO | 2010/125414 | 11/2010 |
| WO | 2011/043381 | 4/2011 |
| WO | 2011/043387 | 4/2011 |
| WO | 2011/092290 | 8/2011 |
| WO | 2011/092293 | 8/2011 |
| WO | 2011/095450 | 8/2011 |
| WO | 2013/160315 | 10/2013 |
| WO | WO 2013/155464 | 10/2013 |
| WO | WO 2013/160317 | 10/2013 |
| WO | WO 2015/112642 | 7/2015 |
| WO | WO 2016/065177 | 4/2016 |
| WO | WO 2016/156576 | 10/2016 |
| WO | WO 2018/102552 | 6/2018 |
| WO | WO 2018/219804 | 12/2018 |
| WO | WO 2019/036503 | 2/2019 |

OTHER PUBLICATIONS

Ambroziak et al., "Cogenital adrenal hyperplasia due to 21-hydroxylase deficiency—management in adults," Polish Journal of Endocrinology, 2010, 61:142-155.

Arlt et al., "Health status of adults with congenital adrenal hyperplasia: a cohort study of 203 patients," J Clin Endocrinol Metab., Nov. 2010, 95(11):5110-21.

Arvanitis, AG., et al., "Non-Peptide Corticotropin-Releasing Hormone Antagonists: Syntheses and Structure—Activity Relationships of 2-Anilinopyrimidines and -triazines," J. Med. Chem., 1999, 42(5): 805-818.

Auchus et al., "Approach to the patient: the adult with congenital adrenal hyperplasia," J Clin Endocrinol Metab., Jul. 2013, 98(7):2645-55.

Auchus RJ, et al., "Management of the adult with congenital adrenal hyperplasia," Int J Ped Endocrinol., 2010, Article ID 614107: 1-9.

Bachelot A, et al., "Bone health should be an important concern in the care of patients affected by 21 hydroxylase deficiency," Int J Ped Endocrinol., 2010, Article ID 326275: 1-7.

Bakshi VP, et al., "Reduction of Stress-Induced Behavior by Antagonism of Corticotropin-Releasing Hormone 2 (CRH2) Receptors in Lateral Septum or CRH1 Receptors in Amygdala", J. Neurosci., 2002, 22(7): 2926-2935.

Barreau F. et al., "Pathways involved in gut mucosal barrier dysfunction induced in adult rats by maternal deprivation: corticotrophin-releasing factor and nerve growth factor interplay," Journal of Physiology—London, 2007, 580(1):347-356.

Behan DP et al., "Neurobiology of corticotropin releasing factor (CRF) receptors and CRF-binding protein: implications for the treatment of CNS disorders," Molecular Psychiatry, 1996, 1(4):265-277.

Belza, "Comparison of self-reported fatigue in rheumatoid arthritis and controls," J Rheumatol., Apr. 1995, 22(4):639-643.

Bleicken B, et al., "Improvement of health-related quality of life in adult women with 21-hydroxylase deficiency over a seven-year period," Endocr J., 2012, 59(10):931-939.

Bonfig W. et al., "Hydrocortisone Dosing During Puberty in Patients With Classical Congenital Adrenal Hyperplasia: An Evidence-Based Recommendation," J Clin Endocrinol Metab., 2009, 94(10):3882-3888.

Bonfig et al., "Reduced final height outcome in congenital adrenal hyperplasia under prednisone treatment: deceleration of growth velocity during puberty," J Clin Endocrinol Metab., May 2007, 92(5):1635-1639.

Bornstein et al., "Chronic effects of a nonpeptide corticotropin-releasing hormone type I receptor antagonist on pituitary-adrenal function, body weight, and metabolic regulation," Endocrinology, 1998, 139(4):1546-1555.

Brazier et al., "Validating the SF-36 health survey questionnaire: new outcome measure for primary care," BMJ, Jul. 1, 19928, 305(6846):160-164.

Brunson KL, et al., "Corticotropin-Releasing Hormone (CRH) Downregulates the Function of Its Receptor (CRF1) and Induces CRF1 Expression in Hippocampal and Cortical Regions of the Immature Rat Brain," Experimental Neurology, 2002, 176(1): 75-86.

CAS Registry No. 321839-75-2, Feb. 15, 2001, 1 page.

Chakhtoura Z. et al., "Impact of total cumulative glucocorticoid dose on bone mineral density in patients with 21-hydroxylase deficiency," Eur J Endocrinol., 2008, 158(6):879-887.

Charmandari et al., "Bioavailability of oral hydrocortisone in patients with congenital adrenal hyperplasia due to 21-hydroxylase deficiency," J Endocrinol, Apr. 2001, 169(1):65-70.

Chatzaki, E, et al., "CRF receptor type 1 and 2 expression and anatomical distribution in the rat colon," Journal of Neurochemistry, 2004, 90: 309-316.

Chen C, et al., "1-Alkyl-3-amino-5-aryl-1H-[1,2,4]triazoles: novel synthesis via cyclization of N-Acyl-S-methylisothioureas with alkylhydrazines and their potent corticotropin-Releasing factor-1 (CRF1) receptor antagonist activities," Bioorganic & Medicinal Chemistry Letters, 2001, 11(24): 3165-3168.

Chen C, et al., "Design and Synthesis of a Series of Non-Peptide High-Affinity Human Corticotropin-Releasing Factor1 Receptor Antagonists," J. Med. Chem., 1996, 39(22): 4358-4360.

Chen C, et al., "Design of 2,5-Dimethyl-3-(6-dimethyl-4-methylpyridin-3-yl)-7-dipropylaminopyrazolo[1,5-a]pyrimidine (NBI 30775/R121919) and Structure-Activity Relationships of a Series of Potent and Orally Active Corticotropin-Releasing Factor Receptor Antagonists," J. Med. Chem., 2004, 47(19): 4787-4798.

Chen C, et al., "Optimization of 3-phenylpyrazolo[1,5-a]pyrimidines as potent corticotropin-releasing factor-1 antagonists with adequate lipophilicity and water solubility" Bioorganic & Medicinal Chemistry Letters, 2004, 14(14): 3669-3673.

Chen C, et al., "NBI 30775 (R121919), an Orally Active Antagonist of the Corticotropin-releasing Factor (CRF) Type-1 Receptor for the Treatment of Anxiety and Depression," Drug Development Research, 2005, 65(4):216-226.

Chen Y, et al., "Cellular and molecular mechanisms of hippocampal activation by acute stress are age-dependent," Molecular Psychiatiy, 2006, 11: 992-1002.

Chen Y, et al., "Modulation of dendritic differentiation by corticotropin-releasing factor in the developing hippocampus," Proceedings of the National Academy of Sciences, 2004, 101(44): 15782-15787.

Chinese Office Action in Chinese Application No. 20158005270.4, dated Oct. 19, 2018, 16 pages (with English Translation).

Claahsen-van der Grinten et al., "Prevalence of testicular adrenal rest tumours in male children with congenital adrenal hyperplasia due to 21-hydroxylase deficiency," Eur J Endocrinol., Sep. 2007, 157(3):339-344.

Claustre et al., "Effects of the Vasopressin ($V_{1b}$) Receptor Antagonist, SSR149415, and the Corticotropin-Releasing Factor 1 Receptor Antagonist, SSR125543, on FG 7142-induced Increase in Acetylcholine and Norepinephrine Release in the Rat," Neuroscience, 2006, 141:1481-1488.

Clinicaltrials.gov, "A study in patients with irritable bowel syndrome to measure hormone response after dosing with GW876008 and Gsk561679," U.S. National Library of Medicine, Aug. 6, 2007, retrieved on Jun. 11, 2020, retrieved from URL: https://clinicaltrials.gov/ct2/show/NCT00511563?term=NCT00511563&draw=1&rank=1, 5 pages.

Clinicaltrials.gov, "A study of the effects of a new antidepressant treatment (GSK561679) in females with major depressive disorder," U.S. National Library of Medicine, Aug. 13, 2008, retrieved on Jun. 11, 2020, retrieved from URL: https://clinicaltrials.gov/ct2/show/NCT00733980?term=NCT00733980&draw=2&rank=1, 14 pages.

Clinicaltrials.gov, "A study to compare the putative anxiolytic effect of 2 new drugs in subjects with social anxiety disorder," U.S. National Library of Medicine, Nov. 7, 2007, retrieved on Jun. 11, 2020, retrieved from URL: https://clinicaltrials.gov/ct2/show/NCT00555139?term=NCT00555139&draw=2&rank=1, 10 pages.

Clinicaltrials.gov, "CRF1 antagonist GSK561679 in alcoholism," U.S. National Library of Medicine, Aug. 24, 2010, retrieved on Sep.

(56) References Cited

OTHER PUBLICATIONS 25, 2020, retrieved from URL: https://clinicaltrials.gov/ct2/show/NCT01187511?term=NCT01187511&draw=2&rank=1, 20 pages.

Clinicaltrials.gov, "Evaluation of GSK561679 in women with post-traumatic stress disorder," U.S. National Library of Medicine, Nov. 25, 2009, retrieved on Jun. 11, 2020, retrieved from URL: https://clinicaltrials.gov/ct2/show/NCT01018992?term=NCT01018992&draw=2&rank=1, 9 pages.

Cottone P, et al., "CRF system recruitment mediates dark side of compulsive eating," Proceedings of the National Academy of Sciences, 2009, 106(47): 20016-20020.

Curtis AL, et al., "Pharmacological comparison of two corticotropin-releasing factor antagonists: in vivo and in vitro studies," Journal of Pharmacology and Experimental Therapeutics, 1994, 268(1):359-365.

Dauber et al., "Nocturnal dexamethasone versus Hydrocortisone for the treatment of children with congenital adrenal hyperplasia," Int. J. of Pediatric Endocrinology, 2010, 2010(1):347636.

Deak et al., "The impact of the nonpeptide corticotropin-releasing hormone antagonist antalarmin on behavioral and endocrine responses to stress," Endocrinology, 1999, 140(1):79-86.

Derendorf et al., "Pharmacokinetics and oral bioavailability of hydrocortisone," J Clin Pharmacol. May 1991, 31(5):473-476.

Douma et al., "CRF1 receptor antagonists do not reverse pharmacological disruption of prepulse inhibition in rodents," Psychopharmacology, 2014, 231:1289-1303.

Dournes et al., "Deep brain stimulation in treatment-resistant depression in mice: comparison with the $CRF_1$ antagonist, SSR125543," Progress in Neuro-Psychopharmacology & Biological Psychiatry, 2013, 40:213-220.

Doyon et al., "Effects of the $CRF_1$ receptor antagonist SSR125543 on energy balance and food deprivation-induced in neuronal activation in obese Zucker rats," J. of Endocrinology, 2007, 193:11-19.

Dudzinska B, et al., "Sexual Well-Being in Adult Male Patients with Congenital Adrenal Hyperplasia," Int J Endocrinol., 2014, ID 469289: 1-9.

Dunn et al., "Physiological and behavioral responses to corticotropin-releasing factor administration: is CRF a mediator of anxiety or stress responses?" Brain Res Brain Res Rev., May-Aug. 15, 1990(2):71-100.

Dyck B, et al., "Potent, Orally Active Corticotropin-Releasing Factor Receptor-1 Antagonists Containing a Tricyclic Pyrrolopyridine or Pyrazolopyridine Core," J. Med. Chem., 2005, 48(12): 4100-4110.

Elnecave et al., "Bone mineral density in girls with classical congenital adrenal hyperplasia due to CYP21 deficiency," J Pediatr Endocrinol Metab., Dec. 2008, 21(12):1155-62.

Elnecave et al., "Bone Mineral Density in Girls with Classical Congenital Adrenal Hyperplasia due to CYP21 Deficiency," Journal of Pediatric Endocrinology & Metabolism, 2008, 21:1155-1162.

Esteban et al., "Daily cortisol production rate in man determined by stable isotope dilution/mass spectrometiy," J Clin Endocrinol Metab., Jan. 1991, 72(1):39-45.

EU Clinical Trials Register, "Abbreviated Style Clinical Study Report," Sanofi-Aventis Group, Sep. 5, 2011, 4 pages.

European Office Action in European Application No. 15702917, dated Aug. 16, 2019, 7 pages.

European Office Action in European Application No. 15702917.4, dated Dec. 9, 2018, 7 pages.

Falhammar et al., "Fertility, sexuality and testicular adrenal rest tumors in adult males with congenital adrenal hyperplasia," Eur J Endocrinol., Mar. 2012, 166(3):441-449.

Falhammar et al., "Fractures and bone mineral density in adult women with 21-hydroxylase deficiency," J Clin Endocrinol Metab. Dec. 2007; 92(12):4643-4649.

Falhammar et al., "Increased mortality in patients with congenital adrenal hyperplasia due to 21-hydroxylase deficiency," J Clin Endocrinol Metab., Dec. 2014, 99(12):E2715-21.

Falhammar et al., "Quality of life, social situation, and sexual satisfaction, in adult males with congenital adrenal hyperplasia," Endocrine., 2014, 47:299-307.

Finkielstain et al., "Clinical Characteristics of a Cohort of 244 Patients with Congenital Adrenal Hyperplasia," J Clin Endocrinol Metab, 2012, 97(12):4429-4438.

Fleck et al., "Binding Kinetics Redefine the Antagonist Pharmacology of the Corticotropin-Releasing Factor Type 1 Receptor," The Journal of Pharmacology and Experimental Therapeutics, 2012, 341(2):518-531.

Forest, "Recent advances in the diagnosis and management of congenital adrenal hyperplasia due to 21-hydroxylase deficiency," Human Reproduction Update, 2004, 10(6): 469-485.

Frederic et al., "Radiosynthesis of [C-11]SSR126374, a new selective CRF1 antagonist," Journal of Labelled Compounds & Radiopharmaceuticals, 2011, 54(1):273.

Gilban D, et al.,. "Health related quality of life of children and adolescents with congenital hyperplasia in Brazil," Health Qual Life Outcomes, 2014, 12:107 (9 pages).

Gilligan et al., "Corticotropin-releasing factor antagonists: recent advances and exciting prospects for the treatment of human diseases," Curr. Opin. in Drug Discov. & Develop., 2004, 7(4)487-497.

Grammatopoulos et al., Functional characteristics of CRH receptors and potential clinical applications of CRH-receptor antagonists, Trends in Endocrinology & Metabolism, 2002, 13(10):436-444.

Griebel et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine Hydrochloride (SSR125543A), a Potent and Selective Corticotrophin-Releasing factor(1) Receptor Antagonist. II. Characterization in Rodent Models of Stress-Related Disorders," J. Pharmacol. Exp, Ther., 2002, 301(1):333-345.

Grigoriadis DE, "Corticotropin-Releasing Factor Receptor Antagonists: Potential Novel Therapies for Human Disease," Celltransmissions, 2003, 19(4): 3-10.

Grigoriadis DE, "The corticotropin-releasing factor receptor: a novel target for the treatment of depression and anxiety-related disorders," Expert Opin. Ther. Targets, 2005, 9(4): 651-684.

Grigoriadis DE, et al., "Drugability of Extracellular Targets: Discovery of Small Molecule Drugs Targeting Allosteric, Functional, and Subunit-Selective Sites on GPCRs and Ion Channels," Neuropsychopharmacology, 2009, 34: 106-125.

Grigoriadis DE, et al., "$^{125}I$-$Tyr^0$-Sauvagine: A Novel High Affinity Radioligand for the Pharmacological and Biochemical Study of Human Corticotropin-Releasing Factor $_{2a}$ Receptors," Molecular Pharmacology, 1996, 50:679-686.

Grigoriadis, DE, et al., "The CRF Receptor Structure, Function and Potential for Therapeutic Intervention," Current Medicinal Chemistry—Central Nervous System Agents, 2001, 1(1): 63-97.

Gross RS, et al., "Design and Synthesis of Tricyclic Corticotropin-Releasing Factor-1 Antagonists," J. Med. Chem., 2005, 48(18): 5780-5793.

Gully et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine Hydrochloride (SSR125543A): A Potent and Selective Corticotrophin-Releasing factor(1) Receptor Antagonist. I. Biochemical and Pharmacological Characterization," J. Pharmacol. Exp, Ther., 2002, 301(1):322-332.

Guo Z, et al., "Design and Synthesis of Tricyclic Imidazo[4,5-b]pyridin-2-ones as Corticotropin-Releasing Factor-1 Antagonists," J. Med. Chem., 2005, 48(16): 5104-5107.

Habib et al., "Oral administration of a corticotropin-releasing hormone receptor antagonist significantly attenuates behavioral, neuroendocrine, and autonomic responses to stress in primates," Proceedings of the National Academy of Sciences, 2000, 97(11):6079-6084.

Han TS, et al., "Glucocorticoid treatment regimen and health outcomes in adults with congenital adrenal hyperplasia," Clin Endocrinol, 2013, 8:197-203.

Han et al., "Quality of life in adults with congenital adrenal hyperplasia relates to glucocorticoid treatment, adiposity and insulin resistance: United Kingdom Congenital adrenal Hyperplasia Adult Study Executive (CaHASE)" Eur J Endocrinol., May 3, 2013, 168(6):887-893.

(56) References Cited

OTHER PUBLICATIONS

Han TS, et al., "Relationship Between Final Height and Health Outcomes in Adults with Congenital Adrenal Hyperplasia: United Kingdom Congenital Adrenal Hyperplasia Adult Study Executive (CaHASE)," J Clin Endocrinol Metab., 2014, 99(8):E1547-E1555.
Han TS, et al., "Treatment and health outcomes in adults with congenital adrenal hyperplasia," Nat Rev Endocrinol., 2014, 10:115-124.
Hanger RL, et al., "International Union of Pharmacology. XXXVI. Current Status of the Nomenclature for Receptors for Corticotropin-Releasing Factor and Their Ligands," Pharmacological Reviews, 2003, 55(1): 21-26.
Heinrichs SC, et al., "Brain Penetrance, Receptor Occupancy and Antistress In Vivo Efficacy of a Small Molecule Corticotropin Releasing Factor Type I Receptor Selective Antagonist," Neuropsychopharmacology, 2002, 27:194-202.
Herdman et al., "Development and preliminary testing of the new five-level version of EQ-5D (EQ-5D-5L)," Qual Life Res., Dec. 2011, 20(10):1727-1736.
Hertzberg et al., "Birth prevalence rates of newborn screening disorders in relation to screening practices in the United States," J Pediatr., Oct. 2011, 159(4):555-560.
Hines et al., "Spatial abilities following prenatal androgen abnormality: targeting and mental rotations performance in individuals with congenital adrenal hyperplasia," Psychoneuroendocrinology, Nov. 2003, 28(8):1010-1026.
Hoare et al., "Mechanism of Corticotropin-Releasing Factor Type I Receptor Regulation by Nonpeptide Antagonists," Molecular Pharmacology, 2003, 63(3):751-756.
Hoare SRJ, et al., "Allosteric Ligands for the Corticotropin Releasing Factor Type 1 Receptor Modulate Conformational States Involved in Receptor Activation," Molecular Pharmacology, 2008, 73(5): 1371-1380.
Hoare SRJ, et al., "Conformational states of the corticotropin releasing factor 1 (CRF1) receptor: detection, and pharmacological evaluation by peptide ligands," Peptides, 2003, 24(12): 1881-1897.
Hoare SRJ, et al., "Ligand Affinity for Amino-Terminal and Juxtamembrane Domains of the Corticotropin Releasing Factor Type I Receptor: Regulation by G-Protein and Nonpeptide Antagonists," Biochemistiy, 2004, 43(13): 3996-4011.
Hoare SRJ, et al., "Single amino acid residue determinants of non-peptide antagonist binding to the corticotropin-releasing factor1 (CRF1) receptor," Biochemical Pharmacology, 2006, 72(2): 244-255.
Huang CQ, et al., "Design and synthesis of 3-(2-pyridyl)pyrazolo[1,5-a]pyrimidines as potent CRF1 receptor antagonists," Bioorganic & Medicinal Chemistiy Letters, 2004, 14(15): 3943-3947.
Huang CQ, et al., "Design, synthesis, and SAR of 2-dialkylamino-4-arylpyrimidines as potent and selective corticotropin-releasing factor1 (CRF1) receptor antagonists," Bioorganic & Medicinal Chemistiy Letters, 2004, 14(9): 2083-2086.
Huang CQ, et al., "Synthesis and SAR of 8-Arylquinolines as potent corticotropin-Releasing factor1 (CRF1) receptor antagonists," Bioorganic & Medicinal Chemistry Letters, 2003, 13(19): 3375-3379.
Huang CQ, et al., "Synthesis of 1-methyl-3-phenylpyrazolo[4,3-b]pyridines via a methylation of 4-phthalimino-3-phenylpyrazoles and optimization toward highly potent corticotropin-releasing factor type-1 antagonists," Bioorganic & Medicinal Chemistry Letters, 2003, 13(19): 3371-3374.
Ising M, et al., "High-Affinity CRF1 Receptor Antagonist NBI-34041: Preclinical and Clinical Data Suggest Safety and Efficacy in Attenuating Elevated Stress Response," Neuropsychopharmacology, 2007, 32:1941-1949.
Israeli Office Action in Israeli Application No. 246783, dated Mar. 9, 2019, 3 pages (with English Translation).
Ivy AS, et al., "Hippocampal Dysfunction and Cognitive Impairments Provoked by Chronic Early-Life Stress Involve Excessive Activation of CRH Receptors," J. Neurosci., 2010, 30(39): 13005-13015.
Japanese Office Action in Japanese Application No. 2016-565135, dated Dec. 11, 2018, 14 pages (with English Translation).
Johannsen et al., "Impaired cognitive function in women with congenital adrenal hyperplasia," J Clin Endocrinol Metab., Apr. 2006, 91(4):1376-1381.
Kiddoo DA, et al., "Impact of state of arousal and stress neuropeptides on urodynamic function in freely moving rats," Am J Physiol Regul Integr Comp Physiol, 2006, 290:R1697-R1706.
Kim et al., "Cardiovascular Disease Risk in Adult Women with Congenital Adrenal Hyperplasia Due to 21-hydroxylase Deficiency," Semin Reprod Med, 2009, 27(4):316-321.
King et al., "Long-Term Corticosteroid Replacement and Bone Mineral Density in Adult Women with Classical Congenital Adrenal Hyperplasia," The Journal of Clinical Endocrinology & Metabolism, 2006, 91(3):865-869.
Koob et al., "Update on Corticotropin-Releasing Factor Pharmacotherapy for Psychiatric Disorders: A Revisionist View," Neuropsychopharmacology Reviews, 2012, 37:308-309.
Kosoyan HP, et al., "The $CRF_1$ receptor antagonist, NBI-35965, abolished the activation of locus coeruleus neurons induced by colorectal distension and intracisternal CRF in rats," Brain Research, 2005, 1056(1):85-96.
Kulshreshtha B, et al., "Pubertal development among girls with classical congenital adrenal hyperplasia initiated on treatment at different ages," Indian J Endocrinol Metab., 2012, 16(4):599-603.
Li et al., "The pharmacology of DMP696 and DMP904, non-peptidergic $CRF_1$ receptor antagonists," CNS Drug Reviews, 2005, 11(1):21-52.
Liapakis G, et al., "Members of CRF Family and their Receptors: From Past to Future," Current Medicinal Chemistry, 2011, 18(17):2583-2600.
Linder et al., "Cortisol production rate in childhood and adolescence," J Pediatr, Dec. 1990, 117(6):892-896.
Liu J, et al., "Corticotropin-Releasing Factor and Urocortin I Modulate Excitatory Glutamatergic Synaptic Transmission," Journal of Neuroscience, 2004, 24(16): 4020-4029.
Loechner et al., "Alternative Strategies for the Treatment of Classical Congenital Adrenal Hyperplasia: Pitfalls and Promises," International Journal of Pediatric Endocrinology, vol. 2010, No. 1, Jun. 8, 2010, Article ID 670960, 10 pages.
Logachev et al., "Congenital Adrenal Hyperplasia: Modern Problems of Terminology and Treatment," Pediatrics, Apr. 19, 2012, 91(3):130-135 pages (with English Translation).
Louis et al., "Antidepressant-like Effects of the Corticotropin-Releasing Factor 1 Receptor Antagonist, SSR125543, and the Vasopressin 1b Receptor Antagonist, SSR149415, in a DRL-72 S Schedule in the Rat," Neuropsychopharmacology, 2006, 31:2180-2187.
Lovenberg TW, et al., "Cloning and characterization of a functionally distinct corticotropin-releasing factor receptor subtype from rat brain," Proceedings of the National Academy of Sciences, 1995, 92(3): 836-840.
Lowe RF, et al., "Rational Design, Synthesis, and Structure-Activity Relationships of Aryltriazoles as Novel Corticotropin-Releasing Factor-1 Receptor Antagonists," J. Med. Chem., 2005, 48(5): 1540-1549.
Maciejewski-Lenoir D, et al., "Selective Impairment of Corticotropin-Releasing Factor1 (CRF1) Receptor-Mediated Function Using CRF Coupled to Saporin," Endocrinology, 2000, 141(2):498-504.
Mackay, KB, et al., "Neuroprotective Effects of the CRF1 Antagonist R121920 after Permanent Focal Ischemia in the Rat," Journal of Cerebral Blood Flow & Metabolism, 2001, 21(10): 1208-1214.
Malouf et al., "Cognitive outcome in adult women affected by congenital adrenal hyperplasia due to 21-hydroxylase deficiency," Horm Res., 2006, 65(3):142-150.
Martinez V, et al., "Central CRF, urocortins and stress increase colonic transit via CRF1 receptors while activation of CRF2 receptors delays gastric transit in mice," J Physiol., 2004, 556.1: 221-234.
Martinez-Aguayo et al., "Testicular adrenal rest tumors and Leydig and Sertoli cell function in boys with classical congenital adrenal hyperplasia," J Clin Endocrinol Metab., Dec. 2007, 92(12):4583-9.

(56) References Cited

OTHER PUBLICATIONS

McCarthy JR, et al., "Recent advances with the CRF1 receptor: design of small molecule inhibitors, receptor subtypes and clinical indications," Curr Pharm Des., 1999, 5(5):289-315.

McCarthy JR, et al., "Chapter 2. Recent Progress in Corticotropin-Releasing Factor Receptor Agents," Annual Reports in Medicinal Chemistry, 1999, 34: 11-20.

Merke et al., "Flutamide, testolactone, and reduced hydrocortisone dose maintain normal growth velocity and bone maturation despite elevated androgen levels in children with congenital adrenal hyperplasia," J Clin Endocrinol Metab., Mar. 2000, 85(3):1114-1120.

Merke et al., "Future directions in the study and management of congenital adrenal hyperplasia due to 21-hydroylase deficiency," Ann. Intern. Med., 2002, 336(4):320-334.

Merke et al., "Management of adolescents with congenital adrenal hyperplasia," Lancet Diabetes Endocrinol., Dec. 2013, 1(4):341-352.

Merke et al., "New ideas for medical treatment of congenital adrenal hyperplasia," Endocrinol. Metab. Clin. North. Am., 2001, 30(1):121-135.

Merke et al., "NIH conference: Future directions in the study and management of cogenital adrenal hyperplasia due to 21-hydroxylase deficiency," Ann. Intern. Med., 2002, 136:320-334.

Meslamani et al., "Computational profiling of bioactive compounds using a target-dependent composite workflow," J. Chem. Inf. Model., 2013, 2322-2333.

Migeon et al., "Congenital Adrenal Hyperplasia Owing to 21-Hydroxylase Deficiency," Endocrinology and Metabolism Clinics of North America, 2001, 30(1):193-206.

Million et al., "The newly developed CRF1-receptor antagonists, NGD 98-2 and NGD 9002, suppress acute stress-induced stimulation of colonic motor function and visceral hypersensitivity in rats," PLOS One, 2013, 8(9):e73749.

Million M, et al., "A novel water-soluble selective CRF1 receptor antagonist, NBI 35965, blunts stress-induced visceral hyperalgesia and colonic motor function in rats," Brain Research, 2003, 985(1):32-42.

Mims et al., "Plasma ACTH in Rats Following Medical Adrenalectomy," Journal of the National Medical Association 69(3):145-147, 1977.

Morikawa S, et al., "Results from 28 years of Newborn Screening for Congenital Adrenal Hyperplasia in Sapporo," Clin Pediatr Endocrinol., 2014, 23(2):35-43.

Muthusamy et al., "Clinical review: Adult height in patients with congenital adrenal hyperplasia: a systematic review and metaanalysis," J Clin Endocrinol Metab., Sep. 2010, 95(9):4161-4172.

Nebesio TD, et al., "Growth and Reproductive Outcomes in Congenital Adrenal Hyperplasia," Int J Pediatr Endocrinol., 2010, Article ID 298937, 1-10.

Nermoen et al., "Subjective health status in men and women with congenital adrenal hyperplasia: a population-based survey in Norway," Eur J Endocrinol., Sep. 2010, 163(3):453-459.

Newfield R.S., "ACTH receptor blockade: A novel approach to treat congenital adrenal hyperplasia, or Cushing's disease," Medical Hypotheses, 2010, 74:705-706.

Okuyama et al., "Receptor Binding, Behavioral, and Electrophysiological Profiles of Nonpeptide Corticotropin-Releasing Factor Subtype 1 Receptor Antagonists CRA1000 and CRA 1001," Journal of Pharmacology and Experimental Therapeutics, 1999, 289(2):926-935.

Overstreet et al., "Antidepressant-like effects of CRF$_1$ receptor antagonist SSR125543 in an animal model of depression," European Journal of Pharmacology, 2004, 497:49-53.

Owens et al., "Physiology and pharmacology of corticotropin-releasing factor," Pharmacol Rev., Dec. 1991, 43(4):425-473.

Pang S, et al., "Congenital adrenal hyperplasia due to 21-hydroxylase deficiency: newborn screening and its relationship to the diagnosis and treatment of the disorder," Screening, 1993, 2:105-139.

PCT International Search Report and Written Opinion in International Appln. No. PCT/US2015/012315, dated Nov. 8, 2016, 6 pages.

Pelleymounter MA, et al., "Role of Corticotropin-Releasing Factor (CRF) Receptors in the Anorexic Syndrome Induced by CRF," Journal of Pharmacology and Experimental Therapeutics, 2000, 293(3):799-806.

Perry SJ, et al., "Distinct Conformations of the Corticotropin Releasing Factor Type 1 Receptor Adopted following Agonist and Antagonist Binding Are Differentially Regulated," J. Biol. Chem., 2005, 280(12): 11560-11568.

Philbert et al., "The CRF$_1$ Receptor Antagonist SSR125543 Attenuates Long-Term Cognitive Deficit Induced by Acute Inescapable Stress in Mice, Independently From the Hypothalamic Pituitary Adrenal Axis," Pharmacology, Biochemistiy, and Behavior, 2012, 10:415-422.

Philbert et al., "The CRF$_1$ Receptor Antagonist SSR125543 Prevents Stress-Induced Cognitive Deficit Associated With Hippocampal Dysfunction: Comparison With Paroxetine and D-cycloserine," Psychopharmacology, 2013, 228:97-107.

Ramos et al., "Drug-induced suppression of ACTH secretion does not promote anti-depressive or anxiolytic effects," Behavioral Brain Research, 2014, 265:69-75.

Rivier CL, et al., "Role of Corticotropin-Releasing Factor Receptors Type 1 and 2 in Modulating the Rat Adrenocorticotropin Response to Stressors," Endocrinology, 2003, 144(6): 2396-2403.

Rivier JE, et al., "Constrained Corticotropin Releasing Factor Antagonists (Astressin Analogues) with Long Duration of Action in the Rat," J. Med. Chem. 1999, 42(16):3175-3182.

Russian Office Action in Russian Application No. 2016133972/15(052775), dated Sep. 26, 2018, 10 pages.

Sarafoglou K, et al., "Impact of Hydrocortisone on Adult Height in Congenital Adrenal Hyperplasia—The Minnesota Cohort," J Pediatr., 2014, 164(5):1141-1146.

Seymour et al., "The pharmacology of CP-154,526, a non-peptide antagonist of the CRH1 receptor: a review," CNS Drug Reviews, 2003, 9(1):57-96.

Silva IN, et al., "Randomised controlled trial of growth effect of hydrocortisone in congenital adrenal hyperplasia," Archives of Disease in Childhood, 1997, 77:214-218.

Soliman et al., "Congenital adrenal hyperplasia complicated by central precocious puberty: linear growth during infancy and treatment with gonadotropin-releasing hormone analog," Metabolism., May 1997, 46(5):513-517.

Somajni et al., "Neuropsychological assessment in prepubertal patients with congenital adrenal hyperplasia: preliminary study," Minerva Pediatr., Feb. 2011, 63(1):1-9.

Speiser et al., "Congenital adrenal hyperplasia due to steroid 21-hydroxylase deficiency: an Endocrine Society clinical practice guideline," J Clin Endocrinol Metab., Sep. 2010, 95(9):4133-60.

Speiser et al., "A Summary of the Endocrine Society Clinical Practice Guidelines on Congenital Adrenal Hyperplasia due to Steroid 21-Hydroxylase Deficiency," International Journal of Pediatric Endocrinology 2010, 2010:494173.

Speiser et al., "Congenital Adrenal Hyperplasia Due to Steroid 21-Hydroxylase Deficiency: An Endocrine Society Clinical Practice Guideline," J Clin Endocrinol Metab., 2010, 95(9):4133-4160.

Spierling et al., "Don't stress about CRF: assessing the translational failures of CRF$_1$ antagonists," Psychopharmacology, 2017, 234(9-10):1467-1481.

Steckler, "Developing small molecule nonpeptidergic drugs for the treatment of anxiety disorders: is the challenge still ahead?" Curr. Topics in Behav. Neurosciences, 2009, 415-428.

Stikkelbroeck et al., "High prevalence of testicular adrenal rest tumors, impaired spermatogenesis, and Leydig cell failure in adolescent and adult males with congenital adrenal hyperplasia," J Clin Endocrinol Metab., Dec. 2001, 86(12):5721-5728.

Surget et al., "Corticolimbic transcriptome changes are state-dependent and region-specific in a rodent model of depression and of antidepressant reversal," Neuropsychopharmacology, 2009, 34:1363-1380.

(56) References Cited

OTHER PUBLICATIONS

Surget et al., "Drug-dependent requirement of hippocampal neurogenesis in a model of depression and of antidepressant reversal," Biol. Psychiatiy, 2008, 64:293-301.
Teitelbaum, "Chronic peripheral administration of corticotropin-releasing factor causes colonic barrier dysfunction similar to psychological stress," Am J Physiol Gastrointest Liver Physiol, 2008, 295: G452-G459.
Tellew et al., "Discovery of NBI-77860/GSK561679, a potent corticotropin-releasing factor ($CRF_1$) receptor antagonist with improved pharmacokinetic properties," Bioorganic & Medicinal Chemistry Letters, 2010, 20(24):7259-7264.
Therrell BL, et al., "Newborn Screening for Congenital Adrenal Hyperplasia," Endocrinol Metab Clin North Am., 2001, 30(1):15-30.
Trakakis et al., "An update to 21-hydroxylase deficient congenital adrenal hyperplasia," Gynecol Endocrinol., Jan. 2010, 26(1):63-71.
Trapp CM, et al. "Recommendations for Treatment of Nonclassic Congenital Adrenal Hyperplasia (NCCAH): an Update," Steroids, 2012, 77(4):342-346.
Trapp et al., "Congenital adrenal hyperplasia: an update in children," Curr Opin Endocrinol Diabetes Obes., 2011, 18(3):166-170.
Urani et al., "The Corticotropin-Releasing Factor 1 Receptor Antagonist, SSR125543, and the Vasopressin 1b Receptor Antagonist, SSR149415, Prevent Stress-Induced Cognitive Impairment in Mice," Pharmacology, Biochemistiy, and Behavior, 2011, 98:425-431.
Vale et al., "Chemical and biological characterization of corticotropin releasing factor," Recent Prog Horm Res., 1983, 39:245-270.
Vale et al., "Characterization of a 41-Residue Ovine Hypothalamic Peptide That Stimulates Secretion of Corticotropin and β-Endorphin," Science, 1981, 213:1394-1397.
Vokl TMK, et al., "Adrenarche and Puberty in Children with Classic Congenital Adrenal Hyperplasia due to 21-Hydroxylase Deficiency," Horm Res Paediatr., 2011, 76(6):400-410.
Vokl TMK, et al., "Obesity Among Children and Adolescents with Classic Congenital Adrenal Hyperplasia due to 21-Hydroxylase Deficiency," Pediatrics, 2006, 117(1):e98-e105.
Webb TR, et al., "Synthesis of benzoylpyrimidines as antagonists of the corticotropin-releasing factor-1 receptor," Bioorganic & Medicinal Chemistry Letters, 2004, 14(15): 3869-3873.
Webster et al., "In Vivo and In Vitro Characterization of Antalarmin, a Nonpeptide Corticotropin-Releasing Hormone (CRH) Receptor Antagonist: Suppression of Pituitary ACTH Release and Peripheral Inflammation," Endocrinology, Jan. 1, 1996, 137(12):5747-5750.
White PC, et al., "Congenital Adrenal Hyperplasia due to 21-Hydroxylase Deficiency," Endocr Rev., 2000, 21(3):245-291.
White PC, et al., "Optimizing Newborn Screening for Congenital Adrenal Hyperplasia," J. Pediatr., 2013, 163:10-12.
Whitten JP, et al., "Rapid Microscale Synthesis, a New Method for Lead Optimization Using Robotics and Solution Phase Chemistry: Application to the Synthesis and Optimization of Corticotropin-Releasing Factorl Receptor Antagonists," J. Med. Chem., 1996, 39(22): 4354-4357.
Wilcoxen K, et al., "Synthesis of 3-phenylpyrazolo[4,3-b]pyridines via a convenient synthesis of 4-amino-3-arylpyrazoles and SAR of corticotropin-Releasing factor receptor type-1 antagonists," Bioorganic & Medicinal Chemistry Letters, 2003, 13(19): 3367-3370.
Williams, "Corticotropin-releasing factor 1 receptor antagonists: a patent review," Expert Opin. Ther. Patents, 2013, 23(8): 1057-1068.
Witchel et al., "Congenital Adrenal Hyperplasia," J. Pediatr. Adolesc. Gynecol., 2011, 24:116-126.
Wong et al., "Increased hepatobiliary clearance of unconjugated thyroxine determines DMP 904-induced alterations in thyroid hormone homeostasis in rats," Toxicological Sciences, 2005, 84(2):232-242.
Wood S, et al., "Depressive and cardiovascular disease comorbidity in a rat model of social stress: a putative role for corticotropin-releasing factor," Psychopharmacology, 2012, 222(2): 325-336.
Wustrow DJ, et al., "Pyrazolo[1,5-a]pyrimidine CRF-1 receptor antagonists," Bioorganic & Medicinal Chemistry Letters, 1998, 8(16): 2067-2070.
Yuan J, et al., "3-Aryl pyrazolo[4,3-d]pyrimidine derivatives: nonpeptide CRF-1 antagonists," Bioorganic & Medicinal Chemistry Letters, 2002, 12(16): 2133-2136.
Zorrilla et al., "Behavioral, biological, and chemical perspectives on targeting CRF(1) receptor antagonists to treat alcoholism," Drug and Alcohol Dependence, (2013), 128(3):175-186.
Zorrilla et al., "The therapeutic potential of CRF1 antagonists for anxiety," Expert Opin. Investig. Drugs, 2004, 13(7):799-828.
Zorrilla, "Progress in corticotropin-releasing factor-1 antagonist development," Drug Discov Today, 2010, 15:371-383.
Zoumakis et al., "Corticotropin-releasing hormone receptor antagonists," European Journal of Endocrinology, 2006, 155(1):S85-S91.
Zoumakis et al., "Corticotropin-releasing hormone receptor antagonists: an update," Pediatric Neuroendocrinology Endocr Dev., 2010, 17:36-43.
Kehne et al., "Therapeutic Utility of Non-Peptidic $CRF_1$ Receptor Antagonists in Anxiety, Depression, and Stress-Related Disorders: Evidence from Animal Models," Pharmacol Ther., Dec. 2010; 128(3):460-487.
Merke et al., "Congenital adrenal hyperplasia," Lancet, 2005, 365:2125-2136.
Shuji Kitagawa, "Beishikku Yakugaku Kyokasho Shiriizu 20 Yakuzaigaku," Basic Pharmaceutical Science Textbook Series 20, Pharmaceutical Science, 2nd print, Kagaku-Dojin Publishing Co., Inc., p. 16-19 (Non-English).
Abdellatif, "Microparticles Formulation as a Targeting Drug Delivery System," J Nanomed Res., 2017, 6(2):00151.
Anthenelli et al., "Sex Differences in the ACTH and Cortisol Response to Pharmacological Probes are Stressor-Specific and Occur Regardless of Alcohol Dependence History," Psychoneuroendocrinology, Aug. 2018, 94:72-82.
Auchus et al., "The Effects of Crinecerfont (NBI-74788), a Novel CRF1 Receptor Antagonist, on Adrenal Androgens and Precursors in Patients with Classic Congenital Adrenal Hyperplasia: Results from A Multiple-Dose Phase 2 Study," J Endocrin Soc., 2020, 4(Supplement 1):OR25-03.
Bale et al., "Overview on Therapeutic Applications of Microparticulate Drug Delivery Systems," Crit Rev Ther Drug Carrier Syst., 2016, 33(4):309-361.
Benedetti et al., "The Biochemical and Neuroendocrine Bases of the Hyperalgesic Nocebo Effect," J Neurosci., Nov. 15, 2006, 26(46):12014-12022.
Buxton et al., "Pharmacokinetics: The Dynamics of Drug Absorption, Distribution, Metabolism, and Elimination," Goodman & Gilman's The Pharmacological Basis of Therapeutics., Brunton L.L. ed., 12th ed. 2011, Chapter 2, 29 pages.
Cheng and Speiser, "Treatment outcomes in congenital adrenal hyperplasia," Adv Pediatr., 2012, 59(1):269-281.
*Neurocrine Biosciences, Inc.*, Petitioner, v. *Spruce Biosciences, Inc.*, Patent Owner, Case No. PGR2021-00088, U.S. Pat. No. 10,849,908, Declaration of Robert M. Carey, M.D., dated May 28, 2021, 154 pages.
El Maouche et al., "Congenital Adrenal Hyperplasia," Lancet., Nov. 11, 2017, 390:2194-2210.
Elder et al., "The utility of sulfonate salts in drug development," Journal of Pharmaceutical Sciences, Jan. 1, 2010, 99(7):2948-2961.
Fahmy et al., "Structure and Function of Small Non-Peptide CRF Antagonists and their Potential Clinical Use," Curr Mol Pharmacol., 2017, 10(4):270-281.
Halper et al., "Health-related quality of life in children with congenital adrenal hyperplasia," Health Qual Life Outcomes., 2017, 15(1):194.
Hamilton, "Needle Phobia: A Neglected Diagnosis," J Fam Pract., Aug. 1995, 41(2):169-175.
Hannah-Shmouni et al., "Genetics of Congenital Adrenal Hyperplasia," Best Pract Res Clin Endocrinol Metab., Apr. 2009, 23(2):181-192.
International Preliminary Report in International Application No. PCT/US2015/012315, dated Jul. 26, 2016, 7 pages.
International Preliminary Report in International Application No. PCT/IB2019/001325, dated Dec. 23, 2020, 15 pages.

(56) References Cited

OTHER PUBLICATIONS

International Search Report and Written Opinion in International Application No. PCT/IB2019/001325, dated Jul. 3, 2020, 24 pages.

Invitation to Pay Fees in International Application No. PCT/IB2019/001325, dated Apr. 17, 2020, 15 pages.

Iranmanesh et al., "Glucose Ingestion Selectively Amplifies ACTH and Cortisol Secretory-Burst Mass and Enhances Their Joint Synchrony in Healthy Men," J Endocrinol and Metab., Sep. 2011, 96(9):2882-2888.

Jain et al., "Spray Drying in Pharmaceutical Industry: A review," Research Journal of Pharmaceutical Dosage Forms and Technology, Apr. 10, 2012, 4(2):74-79.

Katkade et al., "Real world data: an opportunity to supplement existing evidence for the use of long-established medicines in health care decision making," J Multidiscip Healthc., 2018, 11:295-304.

Koelsch et al., "The Impact of Acute Stress on Hormones and Cytokines, and How Their Recovery is Affected by Music-Evoked Positive Mood," Sci Reps., Mar. 2016, 6:1-11.

Medlineplus.gov, "21-Hydroxylase Deficiency," NIH US National Library of Medicine, Updated Aug. 18, 2020 [retrieved Dec. 13, 2021], retrieved from URL<https://medlineplus.gov/genetics/condition/21-hydroxylase-deficiency/>, 6 pages.

Merke et al., "Congenital adrenal hyperplasia: epidemiology, management and practical drug treatment," Paediatr Drugs., 2001, 3(8):599-611.

Merke et al., "Congenital Adrenal Hyperplasia Due to 21-Hydroxylase Deficiency," N Engl J Med., Sep. 24, 2020, 383(13):1248-1261.

No Author, "Neurocrine Biosciences Reports Positive Phase II Data for Crinecerfont in Adults with Congenital Adrenal Hyperplasia at ENDO Online 2020," Neurocrine Biosciences Inc., Jun. 8, 2020, 3 pages.

No Author, "Neurocrine Biosciences to Present New Data Analyses for Crinecerfont in Adults with Classical Congenital Adrenal Hyperplasia at ENDO 2021,"Neurocrine Biosciences Inc., Mar. 20, 2021, 5 pages.

No Author, "Spruce Biosciences Presents Phase 1 and 2 Data for Tildacerfont in Adults with Congenital Adrenal Hyperplasia from Endocrine Society's 2021 Annual Meeting," Spruce Biosciences, Mar. 17, 2021, 2 pages.

No Author, "Assessing the Effects of Food on Drugs in INDs and NDAs—Clinical Pharmacology Considerations Guidance for Industry," U.S. Department of Health and Human Services, Food and Drug Administration, Center for Drug Evaluation and Research (CDER), Feb. 2019, Clinical Pharmacology, 17 pages.

Oray et al., "Long-term effect of glucocorticoids," Expert Opinion on Drug Safety, 2016, 30 pages.

Pang et al., "Worldwide Experience in Newborn Screening for Classical Congenital Adrenal Hyperplasia due to 21-Hydroxylase Deficiency," Pediatrics, 1988, 81(6):866-874.

Rose & Hurst, "Plasma Cortisol and Growth Hormone Responses to Intravenous Catheterization," J Hum Stress., Mar. 1975, 1(1):22-36.

Shargel et al., "Multiple-Dosage Regiments," Applied Biopharmaceutics & Pharmacokinetics, 2012, 6th Edition, 31 pages.

Shargel et al., "Multiple-Dosage Regiments," Applied Biopharmaceutics & Pharmacokinetics, 2016, 7th Edition, 33 pages.

Smith et al., "The role of the hypothalamic-pituitary-adrenal axis in neuroendocrine responses to stress," Dialogues Clin Neurosci., 2006, 8:383-395.

Speiser et al., "Congenital Adrenal Hyperplasia Due to Steroid 21-Hydroxylase Deficiency: An Endocrine Society Clinical Practice Guideline," J Clin Endocrinol Metab., 2018, 103(11):4043-4088.

Stewart et al., "Development of a Biorelevant, Material-Sparing Membrane Flux Test for Rapid Screening of Bioavailability-Enhancing Drug Product Formulations," Mol Pharm., 2017, 14(6):2032-2046.

TheFreeDictionary.Com, "Baseline," available on or before Nov. 7, 2016, via Internet Archive: Wayback Machine URL <https://web.archive.org/web/20161107132345/http:/medical-dictionary.thefreedictionary.com/baseline>, 3 pages.

Turcu et al., "Novel treatment strategies in congenital adrenal hyperplasia," Curr Opin Endocrinol Diabetes Obes., 2016, 23(3):225-232.

Turcu et al., "Single-Dose Study of a Corticotropin-Releasing Factor Receptor-1 Antagonist in Women With 21-Hydroxylase Deficiency," J Clin Endocrinol Metab., Mar. 2016, 101(3):1174-1180.

Turcu et al., "The Next 150 Years of Congenital Adrenal Hyperplasia," J Steroid Biochem Mol Biol., Sep. 2015, 153:63-71.

U.S. Appl. No. 62/545,406, Howerton et al., "Corticotropin Releasing Factor Receptor Antagonists," filed Aug. 14, 2017, 65 pages.

Vickers et al., "Why Use Placebos in Clinical Trials? A Narrative Review of the Methodological Literature," Journal of Clinical Epidemiology, 2000, 53(2):157-161.

Vijayan et al., "Metabolic profile, cardiovascular risk factors and health-related quality of life in children, adolescents and young adults with congenital adrenal hyperplasia," 2019, 32(8):871-877.

Webb et al., "Current and Novel Approaches to Children and Young People with Congenital Adrenal Hyperplasia and Adrenal Insufficiency," Best Pract Res Clin Endocrinol Metab., 2015, 29:449-468.

Witchel et al., "Congenital Adrenal Hyperplasia," J. Pediatr. Adolesc. Gynecol., 2017, 30(5):520-534.

PGR2021-00088, U.S. Pat. No. 10,849,908 B2, May 28, 2021.

Kitagawa et al., "Basic Pharmaceutical Science Textbook Series 20," Pharmaceutical Science, 2nd print, Kagaku-Dojin Publishing Co., Inc., 2012, p. 16-19 (with English translation).

\* cited by examiner

TREATMENT OF CONGENITAL ADRENAL HYPERPLASIA

RELATED APPLICATIONS

Any and all priority claims identified in the Application Data Sheet, or any correction thereto, are hereby incorporated by reference under 37 C.F.R. § 1.57. This application is a continuation of U.S. patent application Ser. No. 17/074,845, filed on Oct. 20, 2020, which is a continuation of U.S. patent application Ser. No. 16/227,127, filed on Dec. 20, 2018, now issued U.S. Pat. No. 10,905,690, which is a continuation of U.S. patent application Ser. No. 15/113,362, filed on Jul. 21, 2016, which is the U.S. National Phase of International Application No. PCT/US2015/012315, filed on Jan. 21, 2015, which claims priority to and the benefit of U.S. Provisional Application No. 61/929,941, filed on Jan. 21, 2014; 61/981,033, filed on Apr. 17, 2014; and 62/069,155, filed on Oct. 27, 2014, the disclosures of which are each incorporated herein by reference in their entireties.

TECHNICAL FIELD

Compositions and methods for treating congenital adrenal hyperplasia are described herein.

BACKGROUND

Congenital adrenal hyperplasia (CAH) is a group of autosomal recessive genetic disorders that result in little or no cortisol biosynthesis. The most frequent form of the disease is 21-hydroxylase deficiency caused by mutations in the CYP21A2 gene located on chromosome 6p21, which accounts for approximately 95% of CAH cases (see, e.g., Speiser et al., *Int. J. Pediatr. Endocrinol.* 2010: 494173 (2010) for a review). These mutations can range from complete loss of enzyme activity required for synthesis of cortisol in the adrenal cortex to a spectrum of partial loss, which results in disease severity that is a direct consequence of a specific mutation. This continuum of 21-hydroxylase deficiency has been broadly classified into salt-wasting and simple-virilizing forms, grouped as classical CAH, and the milder form known as non-classic CAH (NCCAH) or "late-onset" CAH, which is usually diagnosed in late childhood or early adulthood. Non-classic CAH patients are either homozygous or compound heterozygotes, often with a classical CAH allele. These patients have sufficient enzyme activity (>20-50% of normal) such that they do not have salt-wasting or cortisol deficiency and have normal genitalia at birth, and many remain asymptomatic throughout life (Trapp et al., Steroids 77(4): 342-46 (2012)). In the less frequent form of the disease, which accounts for 5% of cases, mutation of the 11β-hydroxylase gene CYP11B1 results in CAH (11β-OH CAH).

Both genetic mutations result in congenital adrenal hyperplasia, cortisol deficiency and excessive adrenocorticotropic hormone (ACTH) production with overproduction of androgens. These patients require lifelong management with glucocorticoids and the attendant problems associated with such treatment. Accordingly, a significant need exists for treatment regimens to improve the health, well-being, quality of life, and to manage related disorders in patient with CAH.

SUMMARY

Corticotropin-releasing factor (CRF) activates the $CRF_1$ receptor, a class B G protein-coupled receptor (GPCR). $CRF_1$ antagonists have the potential to directly inhibit ACTH release in patients with CAH, thereby allowing normalization of androgen production while using lower, more physiologic doses of hydrocortisone, and reducing treatment-associated side effects.

In one embodiment, a method is provided for treating CAH by administering to a subject in need thereof an effective amount of a $CRF_1$ antagonist, including (but not limited to) bedtime administration.

In a more specific embodiment, the $CRF_1$ antagonist has a dissociation half-life ($t_{1/2}$) in excess of 30 minutes, and in another embodiment in excess of 40 minutes, and in another embodiment in excess of 50 minutes.

Embodiment 1. A method for treating Congenital Adrenal Hyperplasia (CAH) by administering to a subject in need thereof a $CRF_1$ receptor antagonist having a dissociation half-life in excess of 30 minutes.

Embodiment 2. The method of Embodiment 1 wherein the $CRF_1$ receptor antagonist has a dissociation half-life in excess of 40 minutes.

Embodiment 3. The method of Embodiment 1 wherein the $CRF_1$ receptor antagonist has a dissociation half-life in excess of 50 minutes.

Embodiment 4. The method of any one of Embodiments 1-3 wherein the $CRF_1$ receptor antagonist is Compound I (NBI-77860; 2,5-dimethyl-3-[2-methyl-4-(methyloxy)phenyl]-N-[(1S)-1-(3-methyl-1,2,4-oxadiazol-5-yl)propyl] pyrazolo[1,5-a]pyrimidin-7-amine).

Embodiment 5. The method of any one of Embodiments 1-3 wherein the $CRF_1$ receptor antagonist is NBI-30775, NBI-34041, SSR-126374, SSR-125543, antalarmin (N-butyl-N-ethyl-2,5,6-trimethyl-7-(2,4,6-trimethylphenyl) pyrrolo[3,2-e]pyrimidin-4-amine), or DMP904.

Embodiment 6. The method of any one of Embodiments 1-5 wherein the $CRF_1$ receptor antagonist is administered at bedtime.

Embodiment 7. The method of any one of Embodiments 1-6 wherein the $CRF_1$ receptor antagonist is administered at or before the expected circadian release of ACTH.

Embodiment 8. The method of Embodiment 7 wherein the $CRF_1$ receptor antagonist is administered 3-4 hours before the expected circadian release of ACTH.

Embodiment 9. A method for reducing 17-OHP and ACTH levels in a subject who has Congenital Adrenal Hyperplasia (CAH), said method comprising administering to the subject a $CRF_1$ receptor antagonist at bedtime.

Embodiment 10. The method of Embodiment 9, wherein the $CRF_1$ receptor antagonist is administered at or before the expected circadian release of ACTH.

Embodiment 11. The method of Embodiment 9 or Embodiment 10, wherein the $CRF_1$ receptor antagonist is administered 3-4 hours before the expected circadian release of ACTH.

Embodiment 12. The method of any one of Embodiments 9-11, wherein the $CRF_1$ receptor antagonist is Compound I (NBI-77860; 2,5-dimethyl-3-[2-methyl-4-(methyloxy)phenyl]-N-[(1S)-1-(3-methyl-1,2,4-oxadiazol-5-yl)propyl] pyrazolo[1,5-a]pyrimidin-7-amine).

Embodiment 13. The method of any one of Embodiments 9-11, wherein the $CRF_1$ receptor antagonist is NBI-30775, NBI-34041, SSR-126374, SSR-125543, antalarmin (N-butyl-N-ethyl-2,5,6-trimethyl-7-(2,4,6-trimethylphenyl) pyrrolo[3,2-e]pyrimidin-4-amine), or DMP904.

Embodiment 14. A $CRF_1$ receptor antagonist for use in treating Congenital Adrenal Hyperplasia (CAH), wherein the $CRF_1$ receptor antagonist has a dissociation half-life in excess of 30 minutes.

Embodiment 15. The $CRF_1$ receptor antagonist of 14, wherein the $CRF_1$ receptor antagonist has a dissociation half-life in excess of 40 minutes.

Embodiment 16. The $CRF_1$ receptor antagonist of Embodiment 14, wherein the $CRF_1$ receptor antagonist has a dissociation half-life in excess of 50 minutes.

Embodiment 17. The $CRF_1$ receptor antagonist of any one of Embodiments 14-16, wherein the $CRF_1$ receptor antagonist is Compound I (NBI-77860; 2,5-dimethyl-3-[2-methyl-4-(methyloxy)phenyl]-N-[(1S)-1-(3-methyl-1,2,4-oxadiazol-5-yl)propyl]pyrazolo[1,5-a]pyrimidin-7-amine).

Embodiment 18. The $CRF_1$ receptor antagonist of any one of Embodiments 14-16, wherein the $CRF_1$ receptor antagonist is NBI-30775, NBI-34041, SSR-126374, SSR-125543, antalarmin (N-butyl-N-ethyl-2,5,6-trimethyl-7-(2,4,6-trimethylphenyl)pyrrolo[3,2-e]pyrimidin-4-amine), or DMP904.

Embodiment 19. The $CRF_1$ receptor antagonist of any one of Embodiments 14-18, wherein the $CRF_1$ receptor antagonist is suitable for administration at bedtime.

Embodiment 20. The $CRF_1$ receptor antagonist of any one of Embodiments 14-19, wherein the $CRF_1$ receptor antagonist is suitable for administration at or before the expected circadian release of ACTH.

Embodiment 21. The $CRF_1$ receptor antagonist of any one of Embodiments 14-20, wherein the $CRF_1$ receptor antagonist is suitable for administration 3-4 hours before the expected circadian release of ACTH.

In other embodiments, the methods and uses described above and herein further comprise reducing the amount of a glucocorticoid or mineralocorticoid by at least 10%, 15%, 20%, 30%, 40%, 50%, 60% from the recommended daily dose of GC (such as hydrocortisone (HC), prednisone, prednisolone, dexamethasone, or fludrocortisone) administered to a full grown subject (e.g., a human subject) who has CAH. In other embodiments, the methods and uses described above and herein further comprise reducing the amount of a glucocorticoid or mineralocorticoid by at least 10%, 15%, 20%, 30%, 40%, 50%, 60% from the recommended daily dose of GC (e.g., hydrocortisone) or mineralocorticoid (e.g., fludrocortisone) administered to a growing subject (e.g., a human subject) who has CAH.

These and other embodiments will be apparent upon reference to the following detailed description. To this end, various references are set forth herein that describe in more detail certain background information, procedures, compounds and compositions, and are each hereby incorporated by reference in their entirety.

Terms not specifically defined herein should be given the meanings that would be given to them by one of skill in the art in light of the disclosure and the context. As used in the specification, however, unless specified to the contrary, the terms have the meaning indicated. Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," an, and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

DETAILED DESCRIPTION

Figure 1:
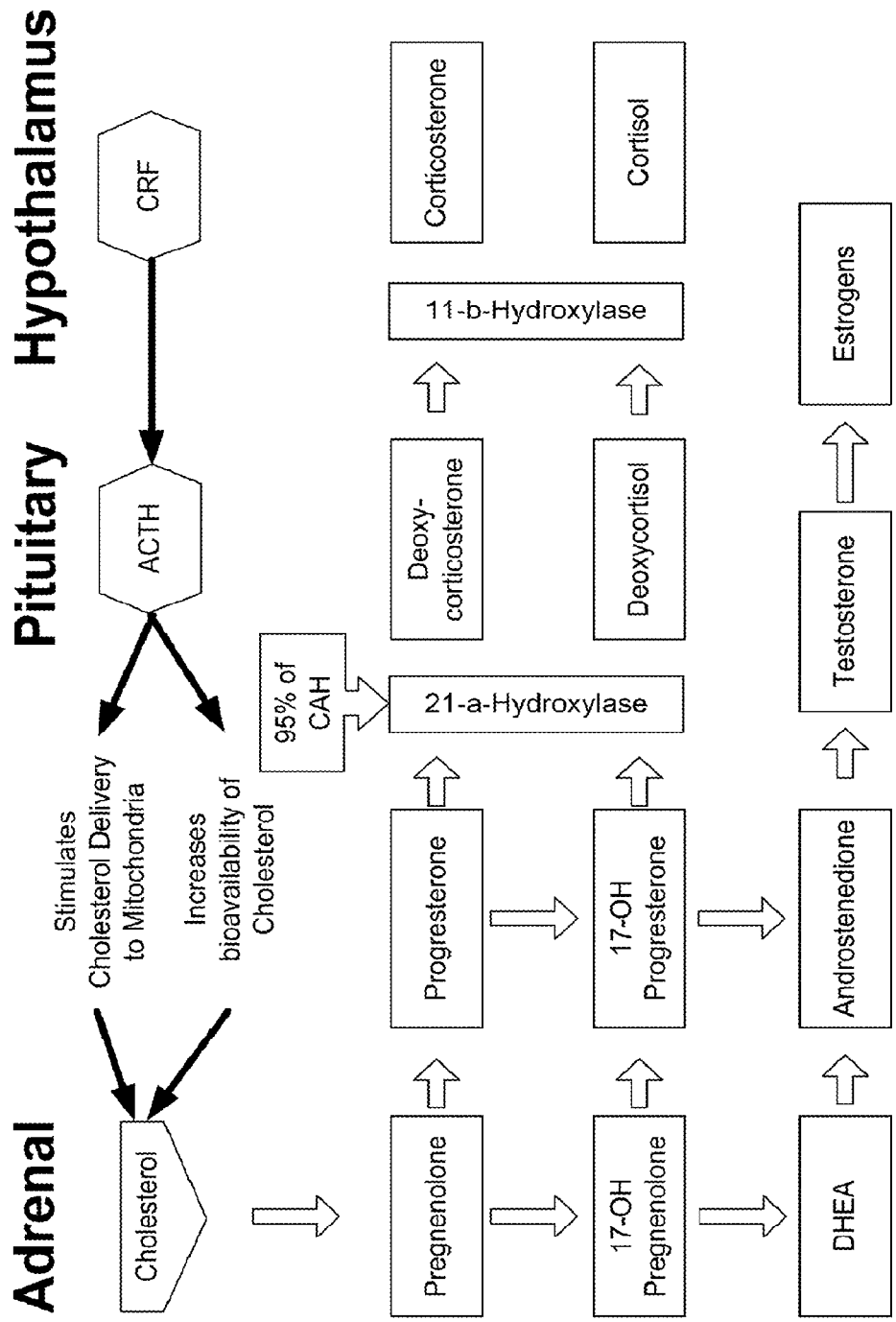
FIG. 1 shows a schematic of steroid synthetic pathways in the adrenal gland. The most common form of CAH is caused by 21-hydroxylase (also called 21-α hydroxylase) deficiency resulting in a decrease of cortisol and increase in androgens such as testosterone and estrogen. A more rare type of classical CAH is 11p-hydroxylase deficiency.

As described herein, $CRF_1$ receptor antagonists have been found to directly inhibit ACTH release in patients with CAH and thereby allow normalization of androgen production.

Administration of a $CRF_1$ receptor antagonist permits use of lower, more physiologic doses of hydrocortisone in subjects with CAH and thus reduces treatment-associated side effects.

Newborn screening for CAH is performed by immunoassay to measure 17-OHP levels in heel-stick capillary blood specimens obtained within the first 72 hours of life. The blood sample is analyzed for 17-OHP by commercially available dissociation-enhanced lanthanide fluoroimmunoassay (DELFIA; PerkinElmer, Waltham Mass.) (White et al., J. Pediatr. 163:10-12 (2013)).

Second-tier screening tests utilizing biochemical and molecular genetic testing methods, performed between 8 and 14 days of life, are employed by nine states in the United States and strongly recommended by an additional 5 states. The biochemical method includes immunoassay with organic solvent extraction or liquid chromatography followed by tandem mass spectrometry to measure steroid ratios of 17-OHP, androstenedione, and 21-deoxycortisol to cortisol (see, e.g., Speiser et al., Int. J. Pediatr. Endocrinol. 2010: 494173, 2010). The genetic screen looks for CYP21A2 mutations that are associated with CAH. While not widely employed in the U.S., the addition of a second screening could potentially improve the sensitivity of the overall screening process, where sensitivity of the first screen alone is approximately 72%.

In absence of results from the newborn screening, female infants with classical CAH are typically identified due to the presence of ambiguous genitalia. Males have normal genitalia at birth and therefore are not diagnosed unless newborn screening is conducted or other medical complications come to attention. Infants who are not initially diagnosed with CAH and suffer from the salt-wasting form of the disease are later diagnosed in the setting of poor weight gain, vomiting, hyperkalemia and hyponatremia within the first few weeks of life.

Treatment of CAH is based on normalization of hormone and steroid levels using a variety of medications from diagnosis in infancy through adulthood. Glucocorticoids are the current standard treatment in CAH and are used both to correct the endogenous cortisol deficiency and for reducing the elevated ACTH levels from the pituitary, which drives increased androgen production. Unlike the treatment of Addison's disease (adrenal insufficiency), in which cortisol replacement is sufficient, the treatment of CAH must also reduce ACTH production, to control the subsequent androgen excess as well. Thus, the goals of glucocorticoid treatment include cortisol replacement and suppression of ACTH to prevent virilization and menstrual disturbances in women and to inhibit testicular adrenal rest tumors in men. Mineralocorticoid replacement is needed to achieve normal plasma renin activity for maintenance of regular blood pressure, electrolyte balance, and volume status in those patients with the salt-wasting form of CAH.

The regimen of glucocorticoid treatment must support normal physiology and also ensure that sufficient cortisol is available during events that may elicit a strong stress response (e.g., intercurrent illness, exercise, hypotension). Careful monitoring is also necessary to avoid the development of iatrogenic Cushing's syndrome due to glucocorticoid overtreatment in an effort to adequately suppress androgen production, or Addisonian syndrome due to undertreatment. Overtreatment with mineralocorticoids may cause hypertension while under-treatment may lead to low blood pressure, salt loss, fatigue and increased requirements for glucocorticoids. Typical laboratory tests for monitoring treatment efficacy include measurement of plasma concentrations of 17-OHP, androstenedione, testosterone, renin activity, and electrolytes.

Adult patients with CAH have an increased prevalence of risk factors for cardiovascular disease including obesity, hypertension, and insulin resistance (see, e.g., Kim et al., Semin. Reprod. Med. 27(4): 316-21 (2009)). A study of a large cohort of pediatric and adult CAH patients (n=244) demonstrated that patients are prescribed a variety of glucocorticoid treatment regimens yet frequently suffer from poor hormonal control and the aforementioned adverse outcomes (see, e.g., Finkielstain et al., J. Clin. Endocrinol Metab. 97(12): 4429-38 (2012)).

Treatment of CAH includes efforts to normalize the cortisol deficiency with glucocorticoids (usually hydrocortisone in children but often more potent agents with narrow therapeutic indices, such as dexamethasone, in adults) and, if necessary for salt-wasting, mineralocorticoids (usually fludrocortisone). The glucocorticoid doses required to achieve sufficient suppression of excess androgens, however, are usually well above the normal physiologic dose used for cortisol replacement alone as in patients with Addison's disease. This increased exposure to glucocorticoids can lead to iatrogenic Cushing's syndrome, increased cardiovascular risk factors, glucose intolerance, and decreased bone mineral density in CAH patients (see, e.g., Elnecave et al., J. Pediatr. Endocrinol. Metab. 21:1155-62 (2008); King et al., J. Clin. Endocrinol. Metab. 91(3): 8656-59 (2006); Migeon et al., Endocrinol. Metab. Clin. North Am. 30:193-206 (2001)).

Corticotropin-releasing factor (CRF) was isolated from ovine hypothalami and identified as a 41-amino acid peptide. CRF has been found to produce profound alterations in endocrine, nervous, and immune system function. CRF is believed to be the major physiological regulator of the basal and stress-induced release of adrenocorticotropic hormone ("ACTH"), B-endorphin, and other pro-opiomelanocortin ("POMC")-derived peptides from the anterior pituitary (see, e.g., Vale et al., Science 213:1394-1397, 1981). Secretion of CRF causes release of ACTH from corticotrophs in the anterior pituitary via binding to the $CRF_1$ receptor, a member of the class B family of G-protein coupled receptors.

Due to the physiological significance of CRF, the development of biologically-active small molecules having significant $CRF_1$ receptor binding activity and which are capable of antagonizing the $CRF_1$ receptor remains a desirable goal and has been the subject of ongoing research and development for the treatment of anxiety, depression, irritable bowel syndrome, post-traumatic stress disorder, and substance abuse.

The pituitary hormone ACTH, under the control of hypothalamic corticotropin-releasing factor (CRF), stimulates uptake of cholesterol and drives the synthesis of pregnenolone initiating steroidogenesis in the adrenal gland (see FIG. 1). The adrenal cortex is comprised of three zones, which produce distinct classes of hormones many of which are driven by ACTH mobilizing cholesterol through this pathway. Deficiencies in these enzymes as a result of mutation or deletion cause the substrate concentrations to increase. In the most common form of CAH resulting from mutations or deletions in the 21-hydroxylase gene (CYP21A2), potent androgens are produced by the adrenal because of the accumulation of the steroid precursors, progesterone and 17-hydroxyprogesterone (17-OHP). Plasma levels of 17-OHP can reach 10-1000 times the normal concentration in these cases. These increases result in the overproduction of androgens, specifically androstenedione, testosterone, and dihydroxytestosterone causing virilization in females. In addition, 21-hydroxylase deficiency in CAH causes insufficient biosynthesis of glucocorticoids and mineralocorticoids, specifically cortisol and aldosterone. Cortisol is a critical negative feedback regulator of hypothalamic CRF secretion and pituitary ACTH release. The lack of glucocorticoid synthesis and release eliminates the restraint on the hypothalamus and pituitary, which causes ACTH levels to increase. The excessive ACTH stimulation causes hypertrophy of the zona *fasciculata* and zona *reticularis* resulting in adrenal hyperplasia.

In an embodiment, a $CRF_1$ receptor antagonist useful for the treatment of CAH is NBI-77860, 2,5-dimethyl-3-[2-methyl-4-(methyloxy)phenyl]-N-[(1S)-1-(3-methyl-1,2,4-oxadiazol-5-yl)propyl]pyrazolo[1,5-a]pyrimidin-7-amine (also referred to as "Compound I" herein), and which has the following structure.

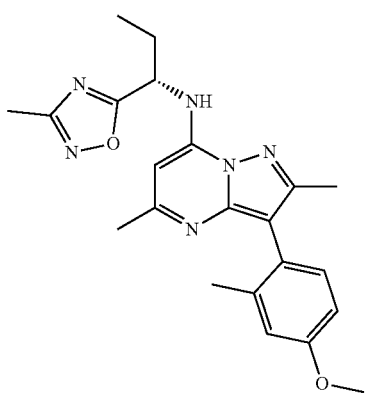

Compound I

Compound I is a potent $CRF_1$ antagonist possessing a binding pKi=8.2 (see, e.g., Tellew et al., *Boorg. Med. Chem. Lett.* 20:7259, 2010 and Int'l. Patent Appl. Publ. No. WO 2006/044958, both of which references are incorporated by reference herein in their entirety). As described herein, Compound I has potent ACTH lowering effects as shown in adrenalectomized rats.

In another embodiment, the $CRF_1$ receptor antagonist useful for the treatment of CAH is a small molecule antagonist as described in U.S. Pat. Nos. 6,586,456, 6,806,282, 6,531,475, 6,664,261, 6,610,678, WO 98/08846, WO 98/11075, WO 99/10350, WO 2000/059888, WO 2006/044821, WO 2006/102194, WO 2006/107784, WO 2006/116412, WO 2006/126718, WO 2007/069565, WO 2007/069671, WO 2008/036541, WO 2008/036579, WO 2008/051533, WO 2008/082003, WO 2008/083070, WO 2008/136377, WO 2009/008552, WO 2009/144632, WO 2010/014280, WO 2010/014687, WO 2010/015628, WO 2010/015655, WO 2010/062718, WO 2010/096426, WO 2011/043387, WO 2011/092293, WO 2011/095450, WO 2011/092290, and WO 2011/043381.

In still another embodiment, the $CRF_1$ receptor antagonist is NBI-30775, CP-316,311, pexacerfont, emicerfont, SSR-125543 [4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine], SSR-126374, ONO-2333, NBI-34041, JNJ-19567470, GSK586529, PF-00572778, CP-376395, antalarmin (N-butyl-N-ethyl-2,5,6-trimethyl-7-(2,4,6-trimethylphenyl)pyrrolo[3,2-e]pyrimidin-4-amine), and DMP904.

In yet another embodiment, the $CRF_1$ receptor antagonist has a dissociation half-life ($t_{1/2}$) in excess of 30 minutes, and in another embodiment in excess of 40 minutes, and in another embodiment in excess of 50 minutes. The dissociation half-life of a particular $CRF_1$ receptor antagonist is determined by the technique disclosed in Example 3. Representative $CRF_1$ receptor antagonists of these embodiments include Compound I, NBI-30775, NBI-34041, SSR-125543A, antalarmin (N-butyl-N-ethyl-2,5,6-trimethyl-7-(2,4,6-trimethylphenyl)pyrrolo[3,2-e]pyrimidin-4-amine), and DMP904.

With respect to the compounds described herein, it should also be understood that when a particular position is designated as hydrogen, that such hydrogen (H) may be replaced with deuterium (D). Incorporation of deuterium in place of hydrogen is known to produce significant effects on the physiological and pharmacological activities of the substituted compound. To this end, it should be understood that deuterium replacement of hydrogen means that the abundance of deuterium at that position is substantially greater than the natural abundance of deuterium. Accordingly, in one embodiment representative compounds include the following.

| Cpd. | Structure | Chemical Name |
|---|---|---|
| NBI-77860 | 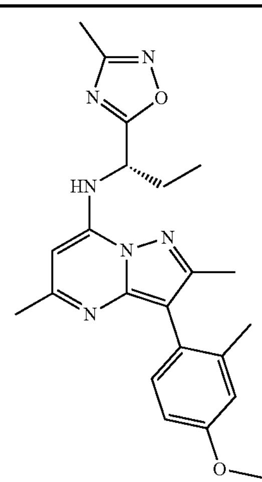 | 2,5-dimethyl-3-[2-methyl-4-(methyloxy)phenyl]-N-[(1S)-1-(3-methyl-1,2,4-oxadiazol-5-yl)propyl]pyrazolo[1,5-a]pyrimidin-7-amine |

-continued

| Cpd. | Structure | Chemical Name |
|---|---|---|
| Deuterated NBI-77860 | | 2,5-dimethyl-3-[2-methyl-4-(d₃-methyloxy)phenyl]-N-[(1S)-1-(3-methyl-1,2,4-oxadiazol-5-yl)propyl]pyrazolo[1,5-a]pyrimidin-7-amine |
| Deuterated NBI-77860 | | 2,5-dimethyl-3-[2-methyl-4-(methyloxy)phenyl]-N-[(1S)-1-(3-d₃-methyl-1,2,4-oxadiazol-5-yl)propyl]pyrazolo[1,5-a]pyrimidin-7-amine |
| Deuterated NBI-77860 | | 2,5-dimethyl-3-[2-methyl-4-(d₃-methyloxy)phenyl]-N-[(1S)-1-(3-d₃-methyl-1,2,4-oxadiazol-5-yl)propyl]pyrazolo[1,5-a]pyrimidin-7-amine |

| Cpd. | Structure | Chemical Name |
|---|---|---|
| Deuterated NBI-77860 | 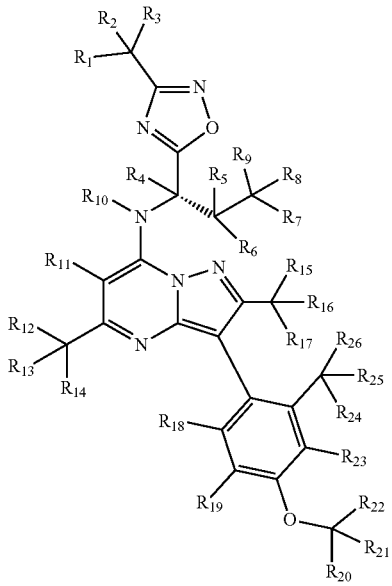<br>$R_1$-$R_{26}$ independently H or D | |
| SSR-125543 | 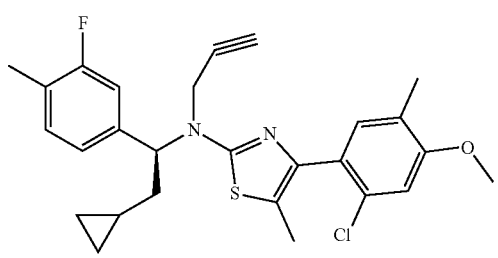 | 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine |
| Deuterated SSR-125543 | 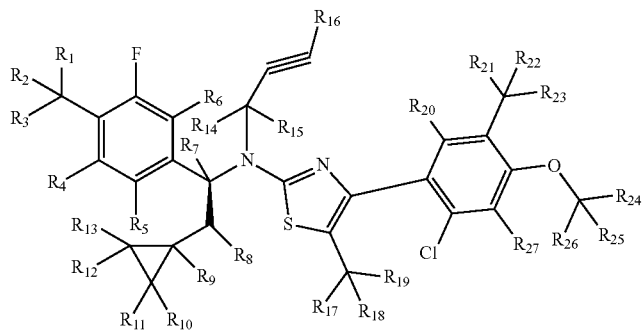<br>$R_1$-$R_{27}$ independently H or D | |

| Cpd. | Structure | Chemical Name |
| --- | --- | --- |
| NBI-30775 | 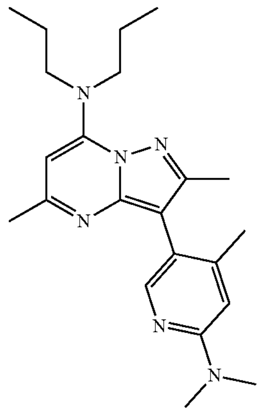 | 5-[7-(dipropylamino)-2,5-dimethylpyrazolo[1,5-a]pyrimidin-3-yl]-N,N,4-trimethylpyridin-2-amine |
| Deuterated NBI-30775 | $R_1$–$R_{32}$ independently H or D | |
| NBI-34041 | 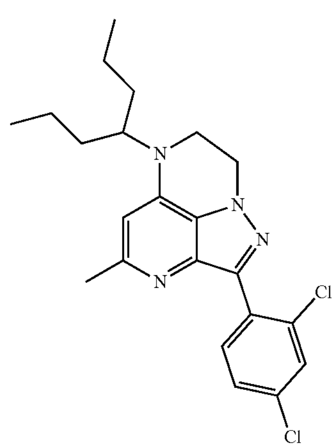 [SMILES: CCCC(CCC)N1CCn2nc(-c3ccc(Cl)cc3Cl)c3nc(C)cc1c32] | 3-(2,4-dichlorophenyl)-9-(heptan-4-yl)-6-methyl-1,2,5,9-tetraazatricyclo[6.3.1.0$^{4,12}$]dodeca-2,4(12),5,7-tetraene |

| Cpd. | Structure | Chemical Name |
|---|---|---|
| Deuterated NBI-34041 | 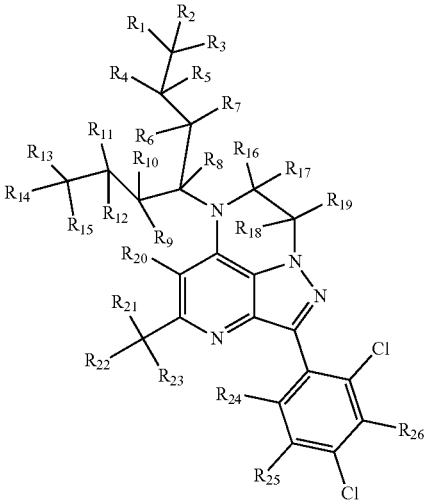 R₁-R₂₆ independently H or D | |
| Pexacerfont | 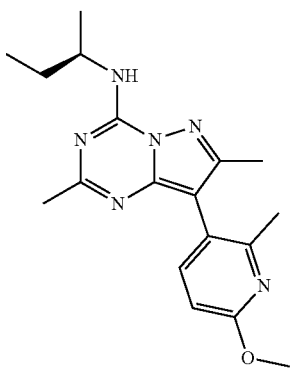 [SMILES: CC[C@@H](C)Nc1nc(C)nc2c(-c3ccc(OC)nc3C)c(C)nn12] | N-[(2R)-butan-2-yl]-8-(6-methoxy-2-methylpyridin-3-yl)-2,7-dimethylpyrazolo[1,5-a][1,3,5]triazin-4-amine |
| Deuterated Pexacerfont | 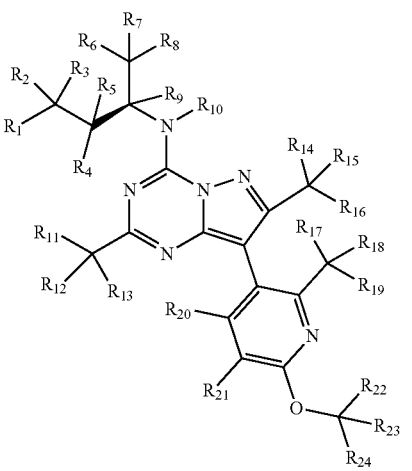 R₁-R₂₄ independently H or D | |

| Cpd. | Structure | Chemical Name |
|---|---|---|
| CP-316,311 | 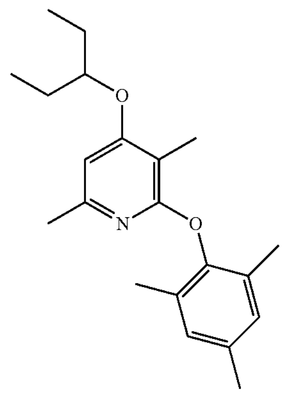 [SMILES: CCC(CC)Oc1cc(C)nc(Oc2c(C)cc(C)cc2C)c1C] | 3,6-dimethyl-4-(pentan-3-yloxy)-2-(2,4,6-trimethylphenoxy)pyridine |
| Deuterated CP-316,311 | R₁-R₂₉ independently H or D | |
| GSK876008 | 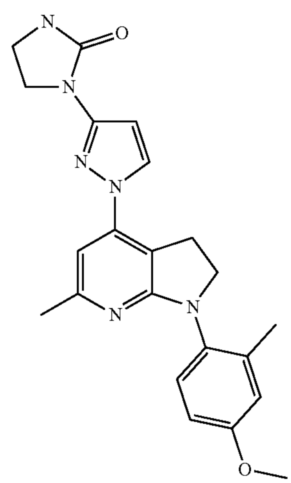 [SMILES: COc1ccc(N2CCc3c(-n4ccc(N5CCNC5=O)n4)cc(C)nc32)c(C)c1] | |

-continued
| Cpd. | Structure | Chemical Name |
|---|---|---|
| Deuterated GSK876008 | 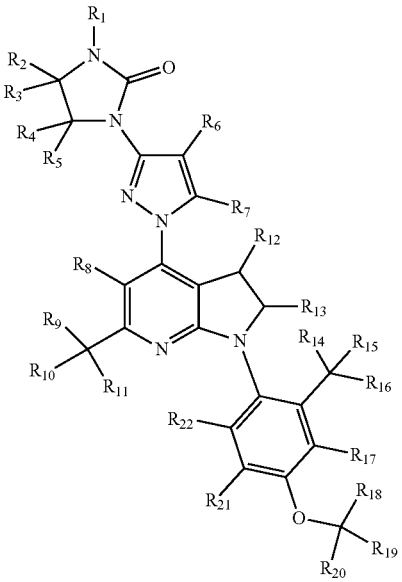 R₁-R₂₂ independently H or D | |
| CRA5626/ R317573 | 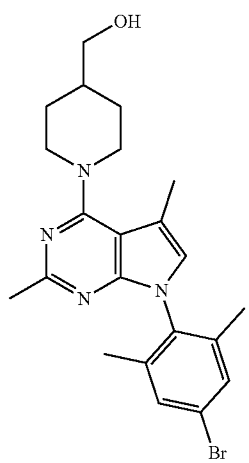 | |
| Deuterated CRA5626/ R317573 | R₁-R₂₄ independently H or D | |

-continued
| Cpd. | Structure | Chemical Name |
|---|---|---|
| ONO2333Ms | 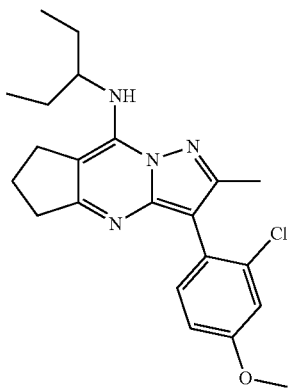 [SMILES: CCC(CC)Nc1c2c(nc3c(-c4ccc(OC)cc4Cl)c(C)nn13)CCC2] | 10-(2-chloro-4-methoxyphenyl)-11-methyl-N-(pentan-3-yl)-1,8,12-triazatricyclo[7.3.0.0$^{3,7}$]dodeca-2,7,9,11-tetraen-2-amine |
| Deuterated ONO2333 | 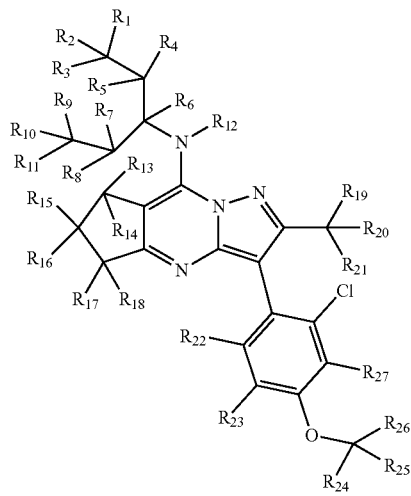<br>$R_1$-$R_{27}$ independently H or D | |
| NBI76169 | 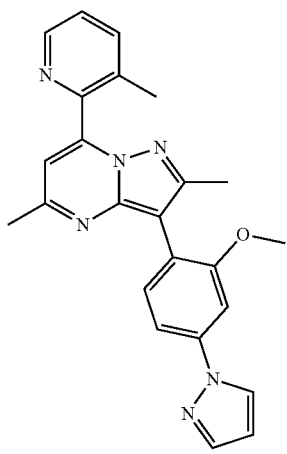 | |

| Cpd. | Structure | Chemical Name |
|---|---|---|
| Deuterated NBI76169 | 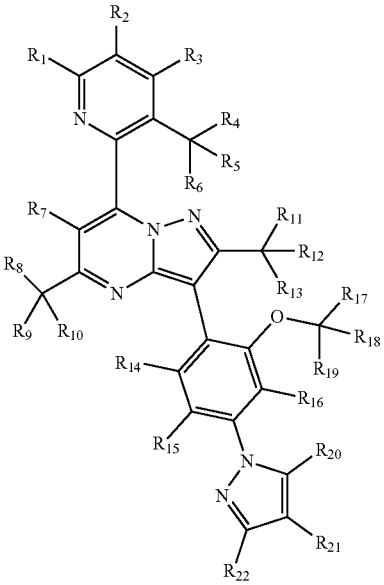 $R_1$-$R_{22}$ independently H or D | |

In another embodiment, any of the aforementioned compounds may incorporate stable or radioactive isotopes. Accordingly, also contemplated is use of isotopically-labeled compounds identical to those described herein, wherein one or more atoms are replaced by an atom having an atomic mass or mass number different from the atomic mass or mass number usually found in nature. Examples of isotopes that can be incorporated into these compounds include isotopes of hydrogen, carbon, nitrogen, oxygen, phosphorous, fluorine and chlorine, such as, but not limited to deuterium as discussed above (2H), as well as 3H, 13C, 14C, 15N, 18O, 17O, 31P, 32P, 35S, 18F, and 36Cl, respectively. Certain isotopically-labeled compounds, for example those into which radioactive isotopes such as 3H and 14C are incorporated, are also useful in drug or substrate tissue distribution assays. Tritiated hydrogen (3H) and carbon-14 (14C) isotopes are particularly preferred for their ease of preparation and detectability. Substitution with heavier isotopes such as deuterium (2H) can provide certain therapeutic advantages resulting from greater metabolic stability, for example increased in vivo half-life or reduced dose requirements and, therefore, may be preferred in some circumstances. Isotopically-labeled compounds can generally be prepared by performing procedures routinely practiced in the art.

Effect on Plasma ACTH in Adrenalectomized Rats

Adrenalectomy eliminates circulating corticosterone (the primary glucocorticoid) in rats and removes the negative feedback control of the HPA axis at both the hypothalamic and pituitary (corticotroph cells) levels and thus chronically elevates plasma ACTH (see, e.g., Mims et al., *J. Natl. Med. Assoc.* 69:145-47 (1977)). Intravenous injection of peptide CRF$_1$ receptor antagonists have been demonstrated to reduce the high plasma ACTH levels in adrenalectomized (ADX) rats (see, e.g., Rivier et al., *J. Med. Chem.* 12:42: 3175-82 (1999)). These findings were recapitulated with the small molecule NBI-77860 (Compound I). In adrenalectomized rats, Compound I has potent capability for lowering ACTH. The maximum reduction in ACTH correlated with peak plasma concentrations of NBI-77860; however, the duration of the ACTH-lowering effect exceeded drug plasma exposure. In adrenalectomized rats, a predictable relationship therefore exists between integrated plasma exposure of NBI-77860 and in vivo efficacy following oral administration.

The effectiveness of a compound as a CRF receptor antagonist may be determined by various assay methods. CRF antagonists described herein may be capable of inhibiting the specific binding of CRF to its receptor and consequently antagonizing activities associated with CRF. A compound may be assessed for activity as a CRF antagonist by one or more generally accepted assays including the assay described in the Examples. CRF antagonists useful for the methods described herein include compounds that demonstrate affinity for CRF receptor.

Without wishing to be bound by theory, in the treatment of CAH, CRF receptor antagonists would potentially block the release of ACTH from pituitary corticotrophs, thereby decreasing the production of androgens, and allow a more refined treatment paradigm for replacement of cortisol.

Animal and human studies have shown the pharmacologic effect of Compound I (NBI-77860) on ACTH release. Standard biomarker assessments used by endocrinologists when monitoring treatment efficacy may be used for monitoring the effects of this CRF$_1$ receptor antagonist. Plasma levels of 17-OHP, androstenedione, testosterone, cortisol and ACTH, as well as urinary metabolites of these steroids, are easily measured in both children and adults giving rapid and meaningful data regarding treatment impact.

Pharmaceutical Compositions and Methods of Treatment

The present disclosure further provides for pharmaceutical compositions comprising any one of the CRF antagonist compounds described herein and a pharmaceutically acceptable excipient for use in the methods for treating CAH. A pharmaceutically acceptable excipient is a physiologically and pharmaceutically suitable non-toxic and inactive material or ingredient that does not interfere with the activity of the active ingredient; an excipient also may be called a carrier. The CRF antagonist compounds may be formulated in a pharmaceutical composition for use in treatment or preventive (or prophylactic) treatment (e.g., reducing exacerbation of CAH disease, or occurrence or recurrence of one or more symptoms of the disease). The methods and excipients described herein are exemplary and are in no way limiting. Pharmaceutically acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, Pa. (2005)). Examples of pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition). A subject may be a human or non-human mammal (e.g., rat, mouse, dog, cat, livestock, zoo animal).

Optimal doses may generally be determined using experimental models and/or clinical trials. The optimal dose may depend upon the body mass, weight, or blood volume of the subject. In general, the amount of a compound described herein, that is present in a dose ranges from about 0.1 mg to about 30 mg per kg weight of the subject. In certain embodiments, a single dose is about 50-1000 mg. The use of the minimum dose that is sufficient to provide effective therapy is usually preferred. Subjects may generally be monitored for therapeutic effectiveness by clinical evaluation and using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising at least one of the compounds described herein for treating CAH or a related disease or disorder may depend upon the subject's condition, that is, stage of the disease, severity of symptoms caused by the disease, general health status, as well as age, gender, and weight, and other factors apparent to a person skilled in the medical art. Similarly, the dose of the compound may be determined according to parameters understood by a person skilled in the medical art.

The pharmaceutical compositions described herein that comprise at least one of the CRF$_1$ antagonist compounds described herein may be administered to a subject in need by any one of several routes that effectively deliver an effective amount of the compound. Such administrative routes include, for example, oral, parenteral, enteral, rectal, intranasal, buccal, sublingual, intramuscular, and transdermal. Compositions administered by these routes of administration and others are described in greater detail herein.

Administration of the compounds or compositions disclosed includes nighttime administration or administration prior to sleep (i.e., bedtime administration). As used herein, bedtime administration refers to dosing intended to deliver clinically relevant concentrations of the CRF$_1$ antagonist at or before (such as 2-5 hours before) the expected circadian release of ACTH. Since this ACTH release is typically at 1-2 A.M., and since most orally administered drugs have a Tmax of several hours, dosing at 10 P.M., for example, which is 3-4 hours in advance of the expected circadian release of ACTH is desirable. This same pre-pulse bedtime dosing may be adapted for shift workers (e.g., those who work at night and sleep during the day), in which case administration will not necessarily occur at nighttime. Administration is therefore dependent upon the expected circadian release of ACTH, and can vary depending upon the individual's (i.e., subject, patient) particular work and sleep patterns. In certain embodiments, a CRF$_1$ receptor antagonist described herein (for example, NBI-77860 or any one of NBI-30775, NBI-34041, SSR-126374, SSR-125543, antalarmin (N-butyl-N-ethyl-2,5,6-trimethyl-7-(2,4,6-trimethylphenyl) pyrrolo[3,2-e]pyrimidin-4-amine), or DMP904) is administered between about 2-5 hours prior to (i.e., before, in advance of) the expected circadian release of ACTH. In other embodiments, the CRF$_1$ receptor antagonist is administered to the subject between about 2-4 hours or 3-5 hours prior to the expected circadian release of ACTH. In a more specific embodiment, CRF$_1$ receptor antagonist is administered to the subject between about 3-4 hours prior to the expected circadian release of ACTH.

Also provided herein is a method for reducing 17-OHP and/or ACTH levels in a subject (i.e., patient, individual) who has CAH by administering a CRF$_1$ receptor antagonist. In certain embodiments, the antagonist is administered at or before the expected circadian release of ACTH. In other certain embodiments, the CRF$_1$ receptor antagonist as administered between about 2-4 hours or between about 3-5 hours prior to the expected circadian release of ACTH. In a more specific embodiment, CRF$_1$ receptor antagonist is administered to the subject between about 3-4 hours prior to the expected circadian release of ACTH.

The methods described herein that comprise administering a CRF$_1$ receptor antagonist to a female subject in need thereof in the manner described herein that causes a decrease in level of ACTH and 17-OHP in the subject may result in decreased release of androgens such as testosterone and androstenedione. The dose of glucocorticoids may concomitantly be decreased by a clinically significant amount, which in turn results in decreased side effects.

The amount of glucocorticoids (GC) and mineralocorticoids (MC) for maintenance therapy in patients who have CAH and who are young and growing and for maintenance therapy in patients who are full grown patients is known to a person skilled in the art. For example, guidelines are described in Speiser et al. (*J. Clin. Endocrinol. Metab.* 95:4133-60 (2010), incorporated by reference in its entirety) and shown in the Tables 1 and 2 therein. Particularly, for young, growing patients who have CAH, persons skilled in the art appreciate that too high dosing with GCs can impede statural growth in the patient. Accordingly, the methods described herein for treating a patient with a $CRF_1$ receptor antagonist may comprise reducing the dose of a GC in a clinically significant manner.

In certain embodiments, methods for treating CAH by administering a $CRF_1$ receptor antagonist may further comprise administering a GC at a dose lower than the currently recommended dose of a GC for treating a subject who has CAH. When the subject is a fully grown patient, the dose of a GC, such as the dose of hydrocortisone (HC), prednisone, prednisolone, dexamethasone, or fludrocortisone recommended for maintenance therapy in a fully grown subject may be decreased by about 10%, 15%, 20%, 30%, 40%, 50%, 60% or more from the recommended doses of 15-25 mg/day HC; 5-7.5 mg/day prednisone, 4-6 mg/day prednisolone; 0.25-0.5 mg/day dexamethasone, or 0.05-0.2 mg/day of fludrocortisone. In a subject who is a growing patient with CAH, the recommended dose of GCs, such as HC may be decreased from the total recommended dose of 10-15 mg/$M^2$ per day and/or the total dose of fludrocortisone of 0.05-0.2 mg/day may each be decreased by about 10%, 15%, 20%, 30%, 40%, 50%, 60% or more in a subject who receives a $CRF_1$ receptor antagonist as described herein. In an embodiment, the methods described herein comprising administering to a subject in need thereof an effective amount of a $CRF_1$ antagonist results in a clinically significant reduction of ACTH levels relative to placebo. In a specific embodiment, administering to a subject in need thereof an effective amount of a $CRF_1$ antagonist results in a clinically significant reduction of ACTH levels relative to placebo, wherein that reduction is at least 25%. In another embodiment, administering to a subject in need thereof an effective amount of a $CRF_1$ antagonist results in a clinically significant reduction of ACTH levels relative to placebo, wherein that reduction is at least 50%. See Speiser et al., supra, for guidelines regarding administering glucocorticoids and mineralocorticoids.

In another embodiment, the methods described herein comprising administering to a subject in need thereof an effective amount of a $CRF_1$ antagonist results in a clinically significant reduction of 17-OHP levels relative to placebo. In another specific embodiment, administering to a subject in need thereof an effective amount of a $CRF_1$ antagonist results in a clinically significant reduction of 17-OHP levels relative to placebo wherein that reduction is at least 25%. In still another embodiment, administering to a subject in need thereof an effective amount of a $CRF_1$ antagonist results in a clinically significant reduction of 17-OHP levels relative to placebo wherein that reduction is at least 50%.

In an embodiment, the methods described herein comprising administering to a subject in need thereof an effective amount of a $CRF_1$ antagonist results in a clinically significant reduction of both ACTH and 17-OHP levels relative to placebo. In a certain embodiment, administering to a subject in need thereof an effective amount of a $CRF_1$ antagonist results in a clinically significant reduction of both ACTH and 17-OHP levels relative to placebo wherein the reduction is at least 25%. In another specific embodiment, administering to a subject in need thereof an effective amount of a $CRF_1$ antagonist results in a clinically significant reduction of both ACTH and 17-OHP levels relative to placebo wherein the reduction is at least 50%.

The pharmaceutical compositions may be in the form of a solution. Alternatively, they may be in the form of a solid, such as powder, tablets, or the like. A composition comprising any one of the compounds described herein may be formulated for sustained or slow release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, at least one of the compounds described herein can be used alone or in combination with appropriate additives to make tablets, powders, granules or capsules, for example, with conventional additives, such as lactose, mannitol, corn starch or potato starch; with binders; with disintegrators; with lubricants; and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in the compositions may be formulated for oral delivery with a flavoring agent, e.g., in a liquid, solid or semi-solid formulation and/or with an enteric coating. Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets.

EXAMPLES

Example 1

CRF Receptor Binding Activity

CRF antagonists as used in the methods described herein may be evaluated for binding activity to the CRF receptor by a standard radioligand binding assay as generally described by Grigoriadis et al. (see, e.g., Mol. Pharmacol vol 50, pp 679-686, 1996) and Hoare et al. (see, e.g., *Mol. Pharmacol* 63: 751-765, 2003.) By utilizing radiolabeled CRF ligands, the assay may be used to evaluate the binding activity of the compounds described herein with any CRF receptor subtype.

Briefly, the binding assay involves the displacement of a radiolabeled CRF ligand from the CRF receptor. More specifically, the binding assay is performed in 96-well assay plates using 1-10 µg cell membranes from cells stably transfected with human CRF receptors. Each well receives about 0.05 mL assay buffer (e.g., Dulbecco's phosphate buffered saline, 10 mM magnesium chloride, 2 mM EGTA)

containing compound of interest or a reference ligand (for example, sauvagine, urocortin I, or CRF), 0.05 mL of [$^{125}$I] tyrosine—sauvagine (final concentration ~150 pM or approximately the $K_D$ as determined by Scatchard analysis) and 0.1 mL of a cell membrane suspension containing the CRF receptor. The mixture is incubated for 2 hours at 22° C. followed by separation of the bound and free radioligand by rapid filtration over glass fiber filters. Following three washes, the filters are dried and radioactivity (Auger electrons from $^{125}$I) is counted using a scintillation counter. All radioligand binding data may be analyzed using the non-linear least-squares curve-fitting programs Prism (GraphPad Software Inc) or XLfit (ID Business Solutions Ltd).

Example 2

CRF$_1$ Receptor Agonist Activity

As reported in Fleck et al. (*J. Pharmacology and Experimental Therapeutics*, 341(2):518-531, 2012) (hereinafter "Fleck et al." and incorporated by reference in it's entirely) the activity of previously identified CRF$_1$ receptor antagonists are presented. Such activity is reported as the kinetically derived affinity ($K_i$) calculated from the association ($k_1$) and dissociation ($k_{-1}$) rate constants by the following equation:

$$K_i = k_{-1}/k_1$$

Also as reported in Fleck et al., the kinetic $K_i$ of the CRF$_1$ receptor antagonists listed in Table 1 below have been reported:

TABLE 1

Representative CRF$_1$ Receptor Antagonists

| Ligand | $k_1$ ($10^6 M^{-1} min^{-1}$) | Kinetic $K_i$ (nM) |
| --- | --- | --- |
| NBI-27914 | 9.4 ± 3 | 25 |
| CP-316,311 | 13 ± 2 | 12 |
| NBI-46200 | 6.2 ± 2 | 22 |
| DMP696 | 7.7 ± 2 | 9.5 |
| pexacerfont | 2.6 ± 0.1 | 19 |
| NBI-35965 | 20 ± 2 | 2.3 |
| ONO-2333Ms | 4.4 ± 2.2 | 15 |
| antalarmin | 3.4 ± 0.6 | 3.9 |
| NBI-34041 | 8.3 ± 2.0 | 1.7 |
| DMP904 | 18 ± 1 | 0.38 |
| NBI-30775 | 14 ± 2.0 | 0.36 |
| SSR125543A | 33 ± 5 | 0.049 |
| NBI-77860 | 0.24 ± 0.05 | 48 ± 9 |

By this same technique, the kinetic $K_i$ of Compound I (NBI-77860) was found to be as follows:

Example 3

Dissociation Half-Life ($T_{1/2}$) of CRF$_1$ Receptor Antagonists

The dissociation half-life ($t_{1/2}$) of a CRF$_1$ receptor antagonist as used in the methods described herein is evaluated by the technique described in Fleck et al. As described therein, the dissociation rate constant for labeled and unlabeled ligands is denoted as $k_{-1}$, while the half-life of drug dissociation from the receptor ($t_{1/2}$), which is equal to the median residence time, is calculated from the dissociation rate constant ($k_{-1}$) by the following equation:

$$t_{1/2} = 0.693/k_{-1}$$

As reported in Fleck et al., the dissociation half-life ($t_{1/2}$) of the CRF$_1$ receptor antagonists listed in Table 2 below have been reported.

TABLE 2

Dissociation Half-Life of Representative Compounds

| Ligand | $k_1$ (min$^{-1}$) | Dissociation $t_{1/2}$ (min) |
| --- | --- | --- |
| NBI 27914 | 0.27 ± 0.07 | 2.6 |
| CP-316,311 | 0.17 ± 0.04 | 4.1 |
| NBI-46200 | 0.13 ± 0.002 | 5.3 |
| DMP696 | 0.095 ± 0.02 | 7.3 |
| pexacerfont | 0.049 ± 0.001 | 14 |
| NBI-35965 | 0.048 ± 0.005 | 16 |
| ONO-2333Ms | 0.063 ± 0.029 | 17 |
| antalarmin | 0.013 ± 0.002 | 53 |
| NBI-34041 | 0.013 ± 0.002 | 53 |
| DMP904 | 0.0072 ± 0.002 | 96 |
| NBI-30775 | 0.0054 ± 0.0006 | 130 |
| SSR125543A | 0.0016 ± 0.0003 | 430 |
| NBI-77860 | 0.012 ± 0.0003 | 58 |

By this same technique, the dissociation half-life of Compound I (NBI-77860) was found to be as follows.

Accordingly, CRF$_1$ receptor antagonists that have a dissociation half-life ($t_{1/2}$) in excess of 30 minutes include (but are not limited to) antalarmin, NBI-34041, DMP904, NBI-30775, SSR125543A, and NBI-77860 (Compound I). These same compounds are also representative of CRF$_1$ receptor antagonists having a dissociation half-life ($t_{1/2}$) in excess of 40 minutes, and a dissociation half-life ($t_{1/2}$) in excess of 50 minutes.

Example 4

Lowering of ACTH in Adrenalectomized Rats

Compound I (NBI-77860)(see, e.g., Tellew et al., *Boorg. Med. Chem. Lett.* 2010, 20:7259; WO2006044958) is a potent CRF$_1$ antagonist possessing a binding pKi of 8.2, a kinetic Ki of 49 nM (Table 1 above), and a Dissociation $t_{1/2}$ of 58 minutes (Table 2 above).

Figure 2:
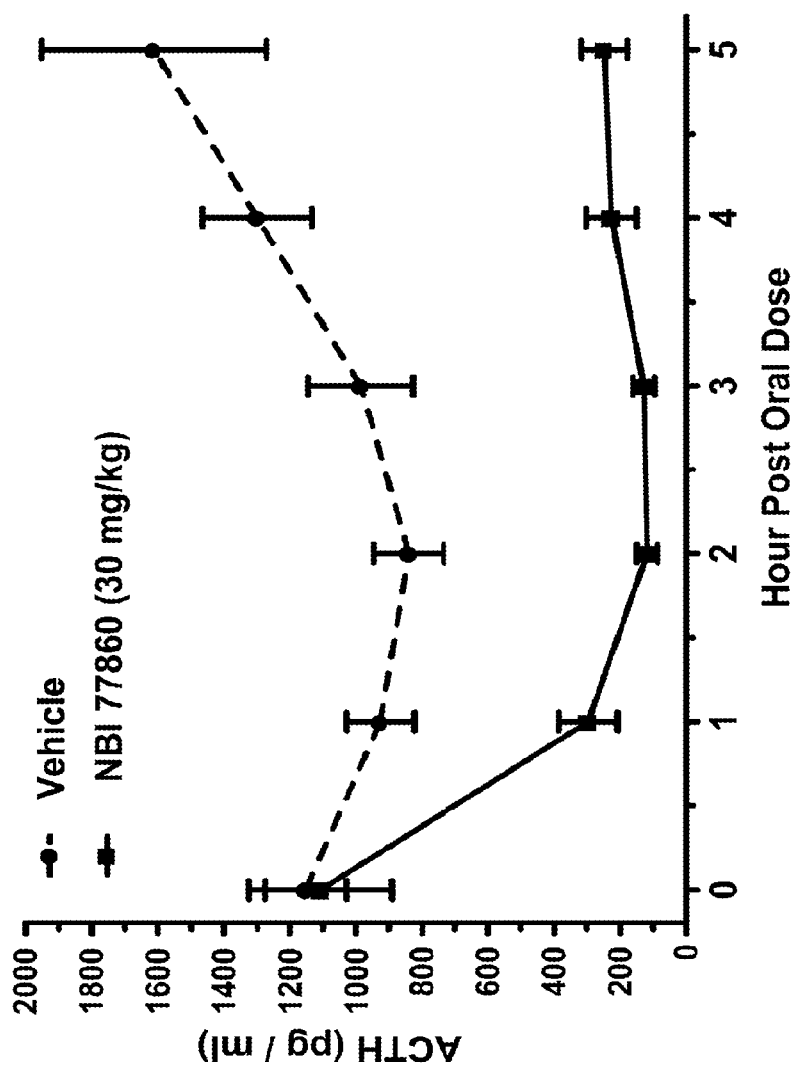
FIG. 2 presents a graph illustrating the effect of Compound I (NBI-77860) on ACTH concentration in adrenalectomized rats. Rats received 30 mg/kg of Compound I (NBI-77860) orally. Data are presented as mean plasma concentration of ACTH (±SEM).

Intravenous injection of peptide CRF$_1$ receptor antagonists have been demonstrated to reduce the high plasma ACTH levels in adrenalectomized (ADX) rats (see, e.g., Rivier et al., *J. Med. Chem.* 12:42:3175-82 (1999)). These findings were recapitulated with the small molecule NBI-77860. When administered orally to ADX rats (n=6/group), 30 mg/kg single doses of NBI-77860 significantly lowered the plasma ACTH levels for up to 5 hours (see FIG. 2). The duration of efficacy correlated with peak plasma concentrations, with a time course exceeding drug plasma exposure. In adrenalectomized rats, a predictable relationship exists between integrated plasma exposure of NBI-77860 and in vivo efficacy following oral administration.

Figure 3A:
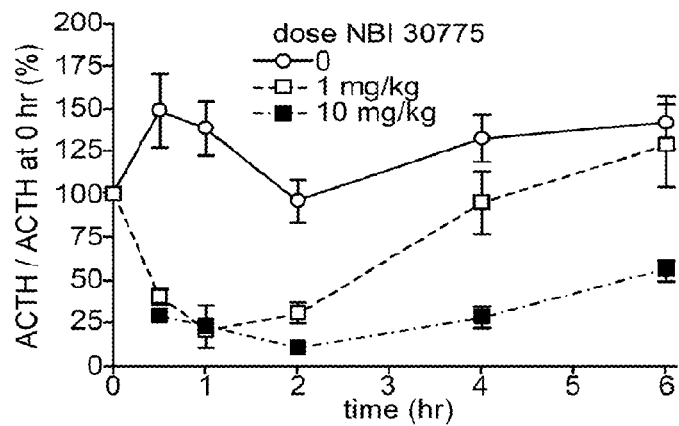
FIGS. 3A-C present graphs illustrating the effect of $CRF_1$ receptor antagonists, differentiated by their dissociation half-life, on ACTH concentration in adrenalectomized rats.
Figure 3B:
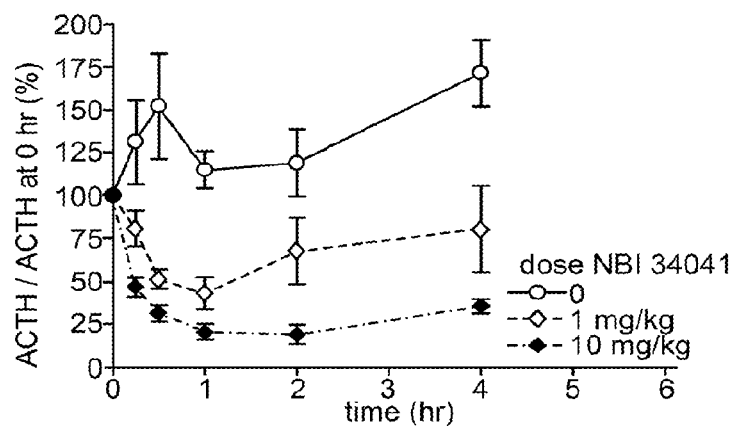
Figure 3C:
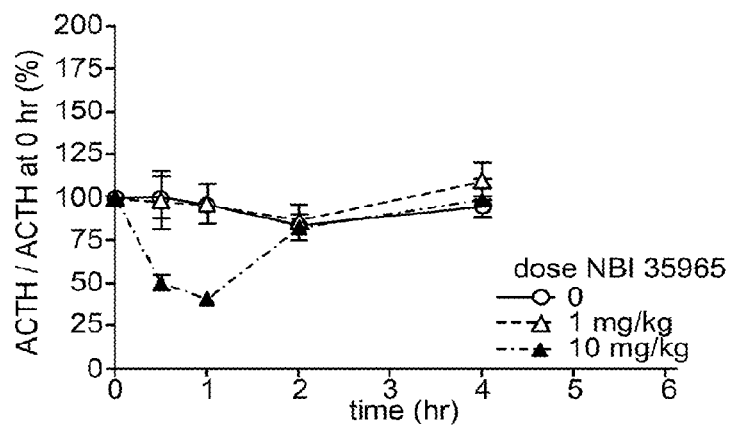

Fleck et al. also report the effects of CRF$_1$ receptor antagonists differentiated by their dissociation half-life on plasma ACTH levels in adrenalectomized rats; namely, NBI 30775, NBI 34041 and NBI 35965. At the highest dose (10 mg/kg), all three ligands reduced ACTH acutely (1 hr post-injection, FIG. 3A-C). After a longer duration, a clear difference emerged between NBI 35965 and the other two ligands. The ACTH level returned to the vehicle level by 2 hr for NBI 35965 (FIG. 3C), whereas the response was sustained for 4-6 hr for NBI 30775 and NBI 34041 (FIGS. 3A and 3B).

Example 5

Pharmacodynamic Effects of Compound I in Humans

In this study, pharmacodynamic effects of NBI-77860 (Compound I) on human subjects were evaluated by observing the effect of single oral doses on HPA axis response produced by metyrapone (0.04 g/kg) with respect to placebo and to a single dose of alprazolam (0.75 mg). Metyrapone blocks cortisol synthesis in the adrenal, thereby mimicking the cortisol deficiency of CAH, and is associated with an acute reflex rise ACTH levels.

The primary analysis was performed by determining the ACTH values between 30 min and 4 h post dose (AUC (30 min to 4 h)). In this analysis, when compared to placebo, the following observations were made. A significant reduction of ACTH AUC (30 min to 4 h) was observed with the alprazolam and the NBI-77860, 400 mg treatments. A non-significant reduction in ACTH AUC (30 min to 4 h) was seen with the NBI-77860, 50 mg treatment. An increase in AUC (30 min to 4 h) was seen with the NBI-77860, 10 mg treatment.

In the analysis performed on the ACTH values between 2 h to 4 h post-dose (AUC (2 h to 4 h))(the period when exposure reached the $C_{max}$ value), there was a significant reduction of ACTH levels in the NBI-77860, 400 mg and 50 mg treatment periods compared with the placebo treatment period; however, the reduction was not seen with the NBI-77860 at the 10 mg dose.

Example 6

Clinical Study

In this study, NBI-77860 (Compound I) was evaluated in the clinical study entitled "A Phase 1, Single-Blind, Placebo-Controlled, Fixed-Sequence, Single-Dose Study to Evaluate the Safety and Tolerability of NBI-77860 in Adult Females with Congenital Adrenal Hyperplasia" (IND 117,388). The study was a single-blind, placebo-controlled, single center, fixed-sequence, single-dose clinical trial in adult female classical CAH patients. It was designed to assess the safety, tolerability, and plasma exposure of NBI-77860, as well as the effect of this compound on endogenous levels of HPA axis hormones.

Figure 4:
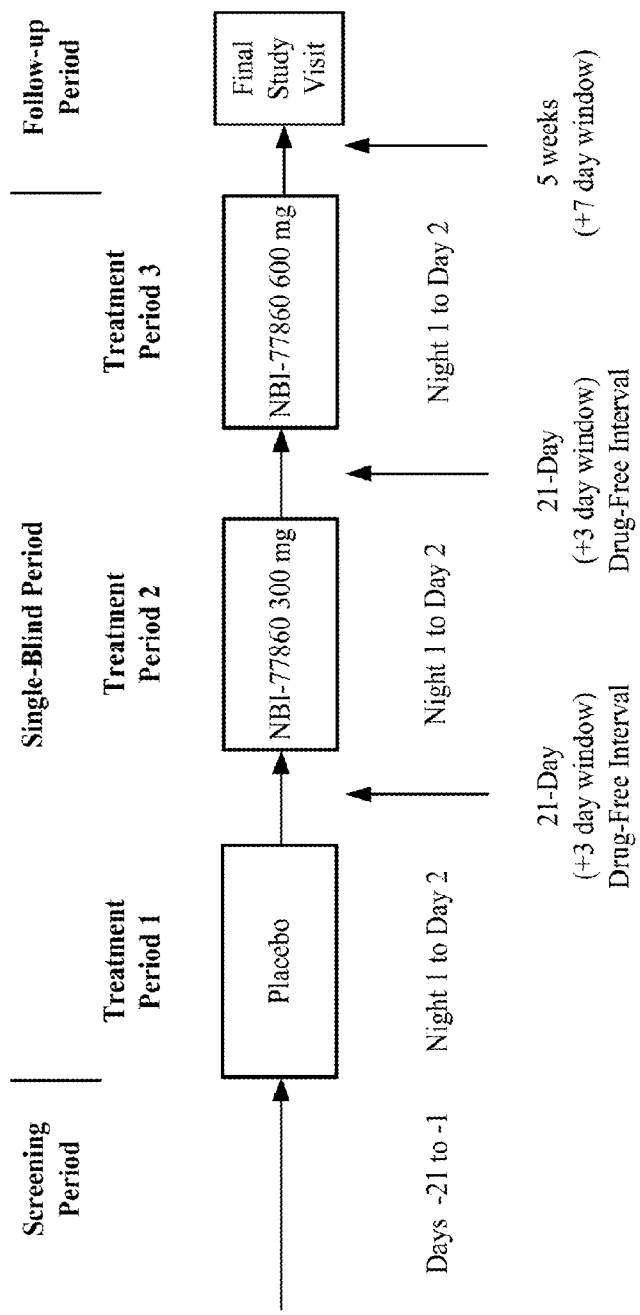
FIG. 4 presents the study design schematic for the clinical trial described in Example 6 that was designed to assess the safety, tolerability and plasma exposure of NBI-77860, as well as the effect of this compound on endogenous levels of HPA (hypothalamic-pituitary-adrenal) axis hormones.

A total of 8 female subjects, ages 19 to 58, with a medical diagnosis of classical 21-hydroxylase deficiency CAH were administered single bedtime doses (hs) of NBI-77860 300 mg, 600 mg, and placebo during three separate treatment periods (see study design schematic in FIG. 4). The subjects' usual morning dose of concurrent steroidal treatment was delayed until after the 16-hour postdose blood samples were collected (i.e., until approximately 1400 h).

Figure 5:
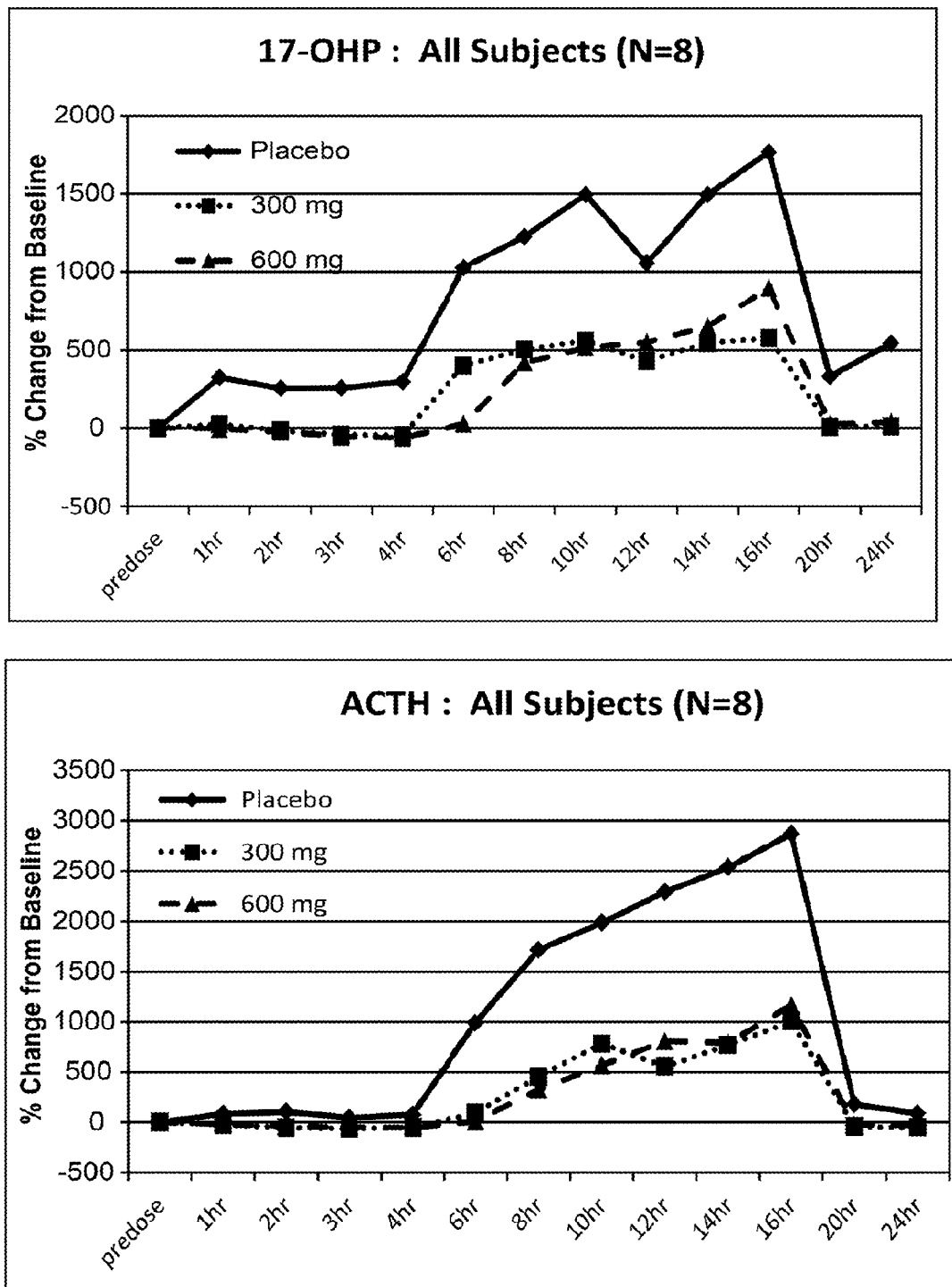
FIG. 5 presents the data for mean 17-OHP (upper panel) and ACTH levels (lower panel) throughout the 24-hour postdose period for the clinical trial described in Example 6.

The PD endpoints for this study included the HPA axis biomarkers of interest in this patient population; namely, 17-hydroxyprogesterone (17-OHP; as the primary PD endpoint), adrenocorticotropic hormone (ACTH), androstenedione, testosterone, and serum cortisol levels. The initial analysis of PD variables was an examination of the grouped subject data for each biomarker, expressed as a mean percent change from predose levels for the two active dosing conditions relative to the placebo condition. The data for mean 17-OHP and ACTH levels throughout the 24-hour postdose period are provided in FIG. 5.

Figure 6:
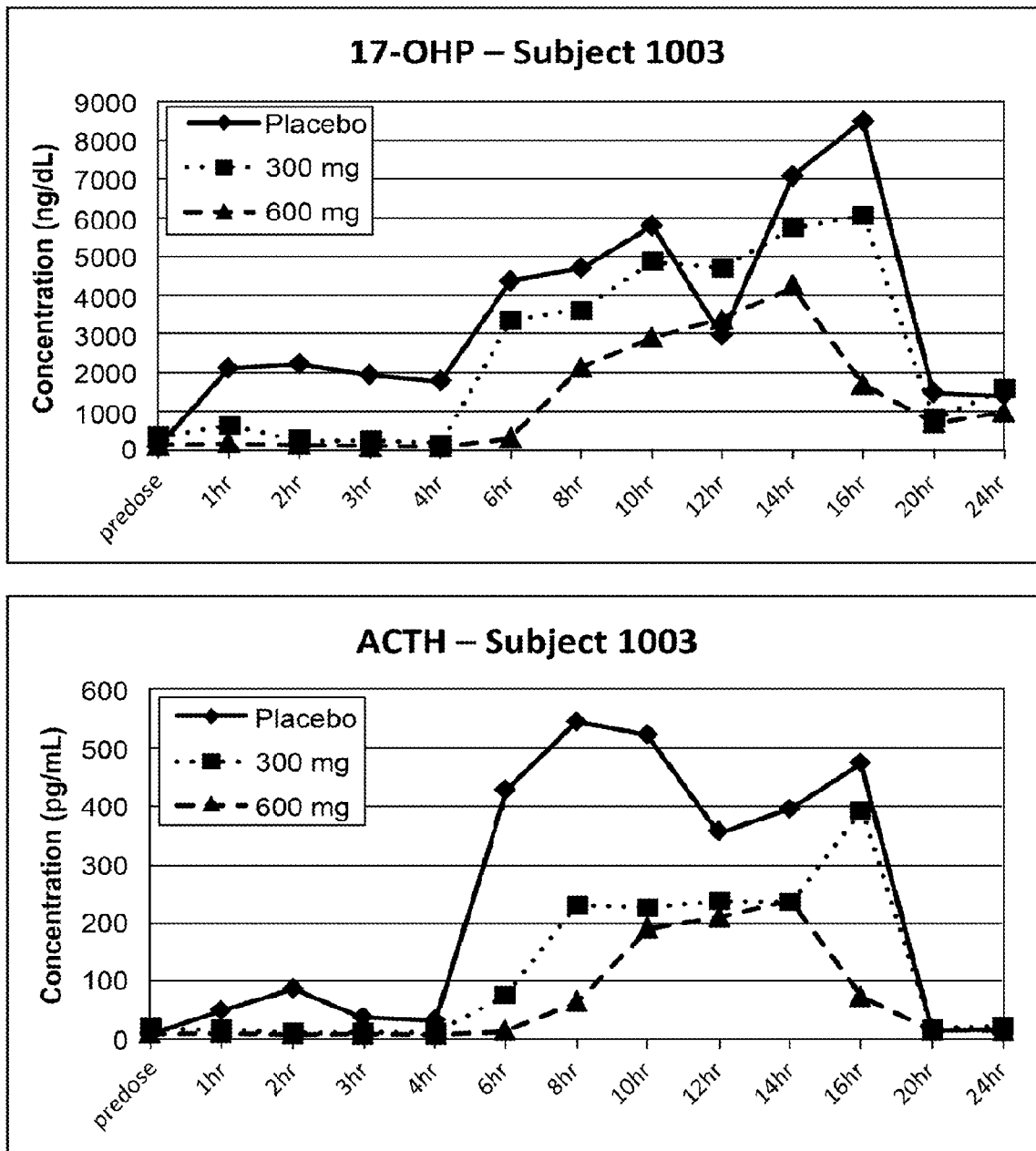
FIG. 6 presents the response of a specific individual subject for 17-OHP (upper panel) and ACTH levels (lower panel) following administration of 300 mg and 600 mg NBI-77860 and placebo over time.

Consistent and clinically meaningful reductions from predose levels of both 17-OHP and ACTH were observed throughout the postdose period following administration of NBI-77860 relative to placebo in these CAH patients. In addition to the group mean data, individual responses were evaluated and treatment "responders" were conservatively defined as those subjects with at least a 50% decrease in 17-OHP and ACTH under active NBI-77860 relative to placebo during the peak morning period. This responder analysis yielded a sizeable responder rate of 50% in the study (none of these subjects were responders during the initial placebo treatment period). Furthermore, the 300 mg dose yielded nearly identical effects on 17-OHP and ACTH as the 600 mg dose. An example of an individual subject response for these biomarkers is provided in FIG. 6.

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet, including U.S. Provisional Application Ser. No. 61/929,941, filed Jan. 21, 2014; U.S. Pat. No. 61/981,033, filed Apr. 17, 2014; and 62/069,155, filed Oct. 27, 2014, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating Congenital Adrenal Hyperplasia (CAH), said method comprising administering to a subject in need thereof already being treated with a glucocortocoid, an effective amount of a $CRF_1$ receptor antagonist, wherein the $CRF_1$ receptor antagonist is 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof.

2. The method of claim 1, wherein the glucocorticoid is hydrocortisone.

3. The method of claim 1, wherein the glucocorticoid is prednisone.

4. The method of claim 1, wherein the glucocorticoid is prednisolone.

5. The method of claim 1, wherein the glucocorticoid is dexamethasone.

6. The method of claim 1, further comprising administering a salt-wasting, mineralocorticoid to the subject.

7. The method of claim 6, wherein the salt-wasting, mineralocorticoid is fludrocortisone.

8. The method of claim 1, wherein the dose of the glucocorticoid is decreased by 10% or more following administration of the $CRF_1$ receptor antagonist.

9. The method of claim 1, wherein the dose of the glucocorticoid is decreased by 15% or more following administration of the $CRF_1$ receptor antagonist.

10. The method of claim 1, wherein the dose of the glucocorticoid is decreased by 20% or more following administration of the $CRF_1$ receptor antagonist.

11. The method of claim 1, wherein the dose of the glucocorticoid is decreased by 30% or more following administration of the $CRF_1$ receptor antagonist.

12. The method of claim 1, wherein the dose of the glucocorticoid is decreased by 40% or more following administration of the $CRF_1$ receptor antagonist.

13. The method of claim 1, wherein the dose of the glucocorticoid is decreased by 50% or more following administration of the $CRF_1$ receptor antagonist.

14. The method of claim 1, wherein the CAH is classical CAH.

15. The method of claim 1, wherein the CAH is caused by 21-α hydroxylase deficiency.

16. The method of claim 1, wherein the CAH is caused by 11β-hydroxylase deficiency.

17. The method of claim 1, wherein the subject has a mutation in the CYP21A2 gene located on chromosome 6p21.

18. The method of claim 1, wherein the subject does not have a mutation of the 11β-hydroxylase gene CYP11B1 (11β-OH CAH).

19. The method of claim 1, wherein the $CRF_1$ receptor antagonist is administered at bedtime.

20. The method of claim 1, wherein the $CRF_1$ receptor antagonist is 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (S SR-125543).

21. The method of claim 1, wherein 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof, is administered in the form of a liquid formulation.

22. The method of claim 1, wherein 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof, is administered in the form of a solid formulation.

23. The method of claim 1, wherein 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof, is administered in the form of a semi-solid formulation.

24. The method of claim 1, wherein 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof, is administered in the form of a tablet, powder, granule or capsule.

25. The method of claim 24, wherein 4-(2-chloro-4-methoxy-5-methylphenyl)-N-[(1S)-2-cyclopropyl-1-(3-fluoro-4-methylphenyl)ethyl]-5-methyl-N-(2-propyn-1-yl)-2-thiazolamine (SSR-125543), or a pharmaceutically acceptable salt thereof, is administered in the form of a capsule.

26. The method of claim 1, wherein the subject is an adult.

27. The method of claim 1, wherein the subject is a child.

28. The method of claim 1, wherein the subject is a female.

* * * * *

UNITED STATES PATENT AND TRADEMARK OFFICE
CERTIFICATE OF CORRECTION

PATENT NO. : 11,311,544 B2
APPLICATION NO. : 17/393553
DATED : April 26, 2022
INVENTOR(S) : Dimitri E. Grigoriadis It is certified that error appears in the above-identified patent and that said Letters Patent is hereby corrected as shown below:

On the Title Page

Column 2, (Item (56) U.S. Patent Documents), Line 10, delete "Father" and insert -- Farber --;

Column 2, (Item (56) Other Publications), Line 3, delete "Form8-K" and insert -- Form 8-K --;

In the Specification

Column 1, Line 16, delete "No." and insert -- Nos. --;

In the Claims

Column 32, Line 40, Claim 1, delete "glucocortocoid," and insert -- glucocorticoid, --;

Column 33, Line 28, Claim 20, delete "(S SR" and insert -- (SSR --.

Signed and Sealed this
Fourteenth Day of June, 2022

Katherine Kelly Vidal
*Director of the United States Patent and Trademark Office*